US007445802B2

(12) United States Patent
Rabinkov et al.

(10) Patent No.: US 7,445,802 B2
(45) Date of Patent: Nov. 4, 2008

(54) SITE-SPECIFIC IN SITU GENERATION OF ALLICIN USING A TARGETED ALLIINASE DELIVERY SYSTEM FOR THE TREATMENT OF CANCERS, TUMORS, INFECTIOUS DISEASES AND OTHER ALLICIN-SENSITIVE DISEASES

(75) Inventors: Aharon Rabinkov, Rehovot (IL); Talia Miron, Kfar Haim (IL); David Mirelman, Ramat Efal (IL); Meir Wilchek, Rehovot (IL)

(73) Assignee: Yeda Research and Development Co. Ltd, Rehovot (IL)

( * ) Notice: Subject to any disclaimer, the term of this patent is extended or adjusted under 35 U.S.C. 154(b) by 594 days.

(21) Appl. No.: 10/451,849

(22) PCT Filed: Dec. 26, 2001

(86) PCT No.: PCT/US01/49384

§ 371 (c)(1),
(2), (4) Date: Dec. 31, 2003

(87) PCT Pub. No.: WO02/058624

PCT Pub. Date: Aug. 1, 2002

(65) Prior Publication Data

US 2004/0115183 A1    Jun. 17, 2004

(30) Foreign Application Priority Data

Dec. 26, 2000   (IL)   ..................................... 140555

(51) Int. Cl.
*A61K 36/8962*   (2006.01)
*A61K 39/00*   (2006.01)
(52) U.S. Cl. .................. 424/754; 424/178.1; 424/182.1; 424/183.1
(58) Field of Classification Search .............. 530/387.1; 514/2
See application file for complete search history.

(56) References Cited

U.S. PATENT DOCUMENTS

| | | | |
|---|---|---|---|
| 4,376,110 A | 3/1983 | David et al. | |
| 4,816,567 A | 3/1989 | Cabilly et al. | |
| 4,946,778 A | 8/1990 | Ladner et al. | |
| 5,091,513 A | 2/1992 | Huston et al. | |
| 5,096,815 A | 3/1992 | Ladner et al. | |
| 5,122,368 A | 6/1992 | Greenfield et al. | |
| 5,137,877 A | 8/1992 | Kaneko et al. | |
| 5,514,554 A | 5/1996 | Bacus | |
| 5,645,835 A | 7/1997 | Fell, Jr. et al. | |
| 5,861,156 A | 1/1999 | George et al. | |
| 5,863,745 A | 1/1999 | Fitzgerald et al. | |
| 5,965,131 A | 10/1999 | Griffiths et al. | |
| 6,008,319 A | 12/1999 | Epstein et al. | |
| 6,299,876 B1 | 10/2001 | Bagshawe | |
| 6,312,694 B1 | 11/2001 | Thorpe et al. | |
| 6,689,588 B1 * | 2/2004 | Mirelman et al. ........... 435/130 |

FOREIGN PATENT DOCUMENTS

| | | |
|---|---|---|
| EP | 0 171 496 A2 | 2/1986 |
| EP | 0 173 494 A2 | 5/1988 |
| EP | 0 184 187 A2 | 6/1988 |
| EP | 0 302 473 A2 | 2/1989 |
| EP | 0 506 124 A1 | 9/1992 |
| EP | 0 554 441 B1 | 1/1999 |
| WO | WO 87/02671 A1 | 5/1987 |
| WO | WO 86/01533 | 3/1988 |
| WO | WO 91/03134 A1 | 6/1991 |
| WO | WO 91/09134 | 6/1991 |
| WO | WO 97/39115 * | 10/1997 |
| WO | WO 97/39115 A1 | 10/1997 |

OTHER PUBLICATIONS

Miron et al (Mol Cancer Ther, 2003, 2:1295-1301).*
Arditti et al (Mol Cancer Ther, 2005, 4:325-331).*
Topp et al (J of Controlled Release, 1998, 53:15-23).*
Badruddoja et al (Frontiers in Bioscience, 2006, 11:1466-1478).*
Hirsch et al (Nutrition and Cancer, 2000, 38:245-254, IDS).*
Stratagene catalog 1988, p. 39.*
Miron et al (Mol Cancer Ther, 2003, 2:1295-1301).*
Arditti et al (Mol Cancer Ther, 2005, 4:325-331).*
"The Totally Garlic Ezine", Jul. 2000, p. 1-6.*
Anon "Sniffing out the benefits of garlic," *Chemistry and Industry* 20: 815 (Oct. 20, 1997), Abstract on Database SCISEARCH on STN, AN 97:86967.
Barone et al. "Isolation, purification, identification, synthesis and kinetics of activity of the anticandidal component of Allium sativum and a hypothesis for its mode of action," *Mycologia* 69 (4): 793-825 (1977), Abstract on Database CAPLUS on STN, AN 1977:594680.
Cavallito et al. "Allicin, the Anitbacterial Principle of Allium Sativum. I. Isolation, physical properties and antibacterial action," *J. Am. Chem. Soc.* 66: 1950-1951 (1944), Abstract on Database CAPLUS on STN, AN 1945:1954.
Cheng et al. "Effect of allithiamine on sarcoma- 180 tumor growth in mice," *T'ai-wan I Hsueh hui Tsa Chih*, 80 (4): 385-393 (1981), Abstract on Database CAPLUS on STN, AN 1981:597366.

(Continued)

*Primary Examiner*—Larry Helms
*Assistant Examiner*—Laura B Goddard
(74) *Attorney, Agent, or Firm*—Browdy and Neimark, PLLC

(57) ABSTRACT

Conjugates of the enzyme alliinase with a protein carrier that targets the alliinase to specific cells are used in combination with alliin to produce allicin at a desired target site. The enzyme converts alliin to allicin at the target site to kill cancer cells or pathogens.

17 Claims, 13 Drawing Sheets

OTHER PUBLICATIONS

Gannon "Garlic shown to be effective therapy for heart conditions," *Drug Topic* 135 (10): 36-39 see especially pate 38 (May 20, 1991).
Hirsch et al. "Effect of Purified Allicin, the Major Ingredient of Freshly Crushed Garlic, on Cancer Cell Proliferation," *Nutrition and Cancer* 28 (2): 245-254, see especially the Abstract, pp. 245-246, 250 and paragraph bridging pp. 252-253 (2000).
Holzhey et al. "Use of allicin-urotropin as an internal drug for the treatment of infection and cancer," *DE 4024155 A1* (Feb. 6, 1992), Abstract on Database CAPLUS on STN, AN 1922:2201109.
Jin et al. "Identification of an Essential Tryptophan Residue in Alliinase from Garlic (*Allium sativum*) by Chemical Modification," *Buil. Korean Chem. Soc.* 22(1):68-76 (2001).
Manabe et al. "Alliinase [S-alk(en)yl-Lcysteine sulfoxide lyase] from *Allium tuberosum* (Chinese chive), Purification, localization, cDNA cloning and heterologous functional expression," *Eur. J. Biochem.* 257: 21-30 (1998).
Sakahara et al. "Immunoscientigraphy of Colorectaq1-Cancer using In-111-labeled monoclonal antibody to mucin," *Cancer Immunology Immunotherapy* 41 (3): 157-161, Abstract on Database SCISEARCH on STN, AN 95:705478.
Springer et al. "Ablation of Human Choriocarcinoma Xenografts in Nude Mice by Antibody-Directed Enzyme Prodrug Therapy (ADEPT) with Three Novel Compounds," *Eur. J. Can.* 27 (11): 1361-1362 and p. 1366, col.1.
Van Damme et al. "Isolation and characterization of alliinase cDNA clones from garlic Alliium sativum L. and related species," *Eur. J. Biochem* (Jun. 18/Aug. 14, 1992) 751-757.
Tzahar et al, "A Hierarchical Network of Interreceptor Interactions Determines Signal Transduction by Neu Differentiation Factor/ Neuregulin and Epiderman Growth Factor," *Molecular and Cellular Biology*, 16(10):5276-5287 (1996).
Van Damme et al, "Isolation and Characterization of Alliinase cDNA Clones from Garlic (Allium Sativum L.) and Related Species," *Eur J. Biochem* 209 (2):751-757 (1992).
Sun, et al, "Chimeric Antibody With Human Constant Regions and Mouse Variable Regions Directed Against Carcinoma-Associated Antigen 17-1A," *Proc Natl. Acad. Sci.* 84: 214-218 (1997).
Stroll et al, "Chemical Investigations on Aliin, the Specific Principle of Garlic," *Adv Enzymol* 11:377-401 (1951).
Stancovski, et al, "Mechanistic Aspects of the Opposing Effects of Monoclonal Antibodies to the ERBB2 Receptor on Tumor Growth," *Proc. Natl. Sci. USA* 88:8691-8695 (991).
Sahagan, et al, "A Genetically Engineered Murine/Human Chimeric Antibody Retains Specificity for Human Tumor-Associated Antigen," *The Journal of Immunology* 137:1066-1074 (1986).
Park et al, "Characteristics of Cell Lines Established from Human Gastric Carcinoma," *Cancer Research* 50:2773-2780 (1990).
Pinkas-Kramarski et al, "Diversification of Neu Differentiation Factor and Epidermal Growth Factor Signaling by Combinatorial Receptor Interactions," *The EMBO Journal* 15(10):4252-2467 (1996).
Rabinkov et al, "Alliinase (Alliin Lyase) from Garlic (Alliium Sativum) is Glycosylated at $ASN^{146}$ and Forms a Complex With a Garlic Mannose-Sepcific Lectin," *Glycoconjugate Journal* 12:690-698 (1995).
Neuberger et al, "A Hapten-Specific Chimaeric IgE Antibody with Human Physiological Effector Function," *Letters to Nature* 314(21):268-270 (1985).
Nag et al, "A Colorimetric Assay for Estimation of Polyethylene Glycol and Polyethylene Glycolated Protein Using Ammonium Ferrothiocyanate," *Analytical Biochemistry* 237: 224-231 (1996).
Morrison et al, "Chimeric Human Antibody Molecules: Mouse Antigen-Binding Domains with Human Constant Region Domains," *Proc. Natl. Acad. Sci. USA* 6851-6855 (1984).
Miron et al, "A Spectrophotometric Assay for Allicin and Alliinase (Alliin Lyase) Activity: Reaction of 2-Nitro-5-Thiobenzoate With Thiosulfinates," *Analytical Biochemistry* 265:317-325 (1998).
Miron et al, "A Simplified Method for the Preparation of Succinimidyl Carbonate Polyethylene Glycol for coupling to Proteins," *Bioconi Chemistry* 4:568-569 (1993).

Meinkoth et al, "Hybridization of Nucleic Acids Immobilized on Solid Supports," *Analytical Biochemistry* 138:267-284 (1984).
Mckinney et al, "A Simple, Non-Chromatographic Procedure to Purify Immunoglobulins from Serum and Ascites Fluid," *Journal of Immunological Methods* 96:271-278 (1987).
Makheja et al, "Antiplatelet Constituents of Garlic and Onion," *Agents and Actions* 29(3/4):360-363 (1990).
Liu et al, "Chimeric Mouse-Human IgG1 Antibody that can Mediate Lysis of Cancer Cells," *Proc. Natl. Acad. Sci. USA* 84:3439-3443 (1987).
Abramovitz et al, "Allicin-Induced Decrease in Formation of Fatty Streaks (Atherosclerosis) in Mice Fed a Cholesterol-Rich Diet," *Coronary Artery Dis* 10:515-519 (1999).
Augusti et al, "Lipid Lowering Effect of Allicin (Diallyl Disulphide-Oxide) on long term feeding to Normal Rats," *Experientia* 30:468-470 (1974).
Better et al, "*Escherichia Coli* Secretion of an Active Chimeric Antibody Fragment," *Science* 240:1041-1043. (1988).
Bordia et al, "The Protective Active of Essential Oils of Onion and Garlic in Cholesterol-Fed Rabbits," *Atherosclerosis* 28:155-159 (1977).
Bordia et al, "Effect of Essential Oil of Garlic on Serum Fibrinolytic Activity in Patients with Coronary Artery Disease," *Atherosclerosis* 28:155-159 (1977).
Bordia et al, "Effect of Garlic Feeding on Regression of Experimental Atherosclerosis in Rabbits," *Artery* 7(5):428-437 (1980).
Boulianne et al, "Production of Functional Chimaeric Mouse/Human Antibody," *Nature* 312:643-646 (1984).
Cabilly et al, "Generation of Antibody Activity from Immunoglobulin Polypeptide Chains Produced in *Escherichia Coli*," *Proc. Natl. Acad. Sci USA* 81:3273-3277 (1984).
Carlsson et al, "Protein Thiolation and Reversible Protein-Protein Conjugation," *Biochem J* 173:723-737 (1978).
Degani et al, "Selective Cyanylation of Sulfhydryl Groupls. II. On the Synthesis of 2-Nitro-5-Thiocyanatobenzoic Acid" *J. Org. chem.*, 36(18):2727-2728 (1971).
Eilat et al, "Alteration of Lipid Profile in Hyperlipidemic Rabbits by Allicin, an Active Constituent of Garlic," *Coronary Artery Dis* 6:985-990 (1995).
Eshhar et al, "Chimeric T Cell Receptor Which Incorporates the Anti-Tumor Specificity of A Monoclonal Antibody with the Cytolytic Activity of T Cells: A Model System for Immunotherapeutical Approach," *Br J Cancer Suppl*, 10:27-29 (1990).
Gross et al, "Expression of Immunoglobulin-T-Cell Receptor Chimeric Molecules as Functional Receptors with Antibody-Type Specificity," *Proc. Natl. Acad. Sci. USA* 86:10024-10028 (1989).
Hirsch et al, "Effect of Purified Allicin, the Major Ingredient of Freshly Crushed Garlic, on Cancer Cell Proliferation," *Nutrition and Cancer* 38(2):245-254 (2000).
Hunter et al, "Preparation of Iodine-131 Labeled Human Growth Hormone of High Activity," *Nature* 194:495-496 (1962).
Hurwitz et al, "Suppression and Promotion of Tumor Growth by Monoclonal Antibodies to ErbB-2 Differentially Correlate with Cellular Uptake," *Proc. Natl. Acad. Sci. USA* 92:3353-3357 (1995).
Jin et al, "Identification of an Essential Tryptophan Residue in Allinase from Garlic (*Allium Sativum*) by Chemical Modification," *Bull Korea Chem Soc* 22(1):68-76 (2001).
Kamisaki et al, "Reduction In Immunogenicity and Clearance Rate of *Escherichia Coli* L-Asparaginase by Modification with Monomethoxpolyethylene Glycol," *J Pharacol Exp Ther* 216:410-414 (1981).
Kiesewetter et al, "Effects of Garlic on Blood Fluidity and Fibrinolytic Activity: A Randomised, Placebo-Controlled, Doubled-Blind Study," *Br J Pract* 69:24-29 (1990).
Kleijnen et al, "Garlic, Onions and Cardiovascular Risk Factors. A Review of the Evidence from Human Experiments with Emphasis on Commerically Available Preparations," *Br. J. Clin. Pharmac.* 28:535-544 (1989).
Kohler et al, "Continuous Cultures of Fused Cells Secreting Anitbody of Predefined Specificity," *Nature* 256-495-497 (1975).

* cited by examiner

F(ab)-Alliinase unit activity/well

F(ab)-Alliinase unit activity/well

SITE-SPECIFIC IN SITU GENERATION OF ALLICIN USING A TARGETED ALLIINASE DELIVERY SYSTEM FOR THE TREATMENT OF CANCERS, TUMORS, INFECTIOUS DISEASES AND OTHER ALLICIN-SENSITIVE DISEASES

FIELD OF THE INVENTION

The present invention relates to conjugates of alliinase with a protein carrier that targets the alliinase to specific cells. The present invention further relates to a method for producing allicin in situ by administering this conjugate followed by administration of alliin.

BACKGROUND OF THE INVENTION

A large spectrum of medicinal properties has been ascribed to garlic (*Allium Sativum L.*), which makes it one of the most popular medicinal herbs. Garlic preparations have been used from ancient times in folk medicine of different countries for a variety of disorders. Recently, there has been a resumption of interest in the therapeutic properties of garlic, and garlic has become the subject of an increasing number of biochemical and clinical studies.

Most of the active ingredients in crushed garlic are sulfur-containing compounds. The major component was identified as allicin (thio-2-propene-1-sulfinic acid S-allyl ester). The intact garlic clove does not contain allicin, but rather contains its odorless precursor alliin (S-allyl-L-cysteine sulfoxide). In garlic cloves, an enzyme (C-S-lyase, known as alliin lyase or alliinase [E.C. 4.4.1.4]) is present that converts alliin to allicin, pyruvate, and ammonia. Alliin and alliinase are found in different compartments of the garlic cloves. When garlic is cut or crushed, the membranes of these compartments are broken so that the enzyme can react with its precursor, alliin.

Allicin is a chemically unstable colorless liquid that it believed to be responsible for both the odor and much of the biological activity ascribed to garlic. Thus, allicin possesses a remarkably broad spectrum of antibiotic activities, including antibacterial activity against a wide range of Gram-negative and Gram-positive aerobic and anaerobic bacteria, as well as antifungal, antiprotozoal, antiviral, antiparasitic, and insecticidal activities. Miron et al (international publicaton WO 97/39115) discloses a biotechnological process for preparing pure allicin in practically unlimited amounts.

Many recent studies have reported the beneficial effects of allicin on cardiovascular risk factors, particularly serum cholesterol and triglyceride levels as well as lipoprotein balance, hypertonia, and thrombogenesis in animals and in humans. These studies consistently demonstrate that allicin can induce an increase in fibrinolytic activity (Bordia et al, 1997; Kieswetter, 1990), inhibit platelet aggregation (Makheja and Bayley, 1990), improve lipid profile including reducing serum cholesterol levels, decreasing blood pressure, and preventing formation of strokes (Augusti and Mathew, 1974; Bordia et al, 1975; Bordia and Verma, 1980; Knipschid and ter-Riet, 1989; Eilat et al, 1995; Abramovitz et al, 1998). The present inventors have also found that allicin has pronounced anticancer potential.

Most of the beneficial and versatile activities of allicin were experimentally demonstrated in vitro. Allicin is a very chemically active molecule, which readily reacts with compounds in the body and disappears within a few minutes after being mixed with blood. In vivo activities of allicin can be defined as unique activities, that is, those exhibited only by allicin itself, and non-unique activities, those which are exhibited by allicin derivatives or secondary products produced from allicin during treatment with allicin. For example, the most valuable intrinsic activity of allicin is its prominent and broad spectrum antibiotic activity. However, this activity has been noted only for allicin and one of its derivatives, ajoene. The activity of allicin against several microorganisms is very important, especially in cases in which effective therapy has still not yet been developed. The cytotoxic properties of allicin are significantly higher than those of other sulfur compounds derived from garlic, and the present inventors have demonstrated that purified allicin was effective against cancer cells in concentrations significantly lower than those effective to kill normal cells (Hirsh et al, 2000).

One of the problems with using allicin as a drug to treat cancer or infectious diseases is that the allicin molecule is very reactive and rapidly becomes inactivated upon reaction with SH-proteins and non-protein thiols. Therefore, it would be highly desirable to provide allicin in a form such that it could exert its beneficial biological properties, including antibacterial and antitumor activities, at the desired site of the body.

SUMMARY OF THE INVENTION

It is an object of the present invention to overcome the aforementioned deficiencies of the prior art.

It is another object of the present invention to maintain allicin biologically active in vivo.

It is another object of the present invention to deliver allicin in vivo to the site at which it should exert its desired biological activity.

The present invention overcomes the problem of in vivo inactivation of allicin by generating allicin in vivo at the site at which it should exert it desired biological activity. For this purpose, the enzyme alliinase, which catalyzes the synthesis of allicin from its precursor alliin, is coupled to a carrier protein which directs the alliinase to a target. The stable conjugate retains both the alliinase enzymatic activity and the epitope binding activity of the carrier protein to antigens or receptors on the surface of cells of interest without damaging the cells. A patient is treated with this conjugate followed by administration of the precursor alliin. At the desired site, the alliin is converted by the alliinase to allicin, leading to inhibition of cell growth at that site.

In one embodiment of the present invention, the targeting carrier is a cell- or tissue-specific monoclonal antibody that recognizes specific receptors on a cell surface, or a derivative of the monoclonal antibody such as a $F(ab)_2$ dimer, a $F(ab)$ monomer, Fv and single chain natural or recombinant Fv.

In one preferred embodiment of the present invention, the monoclonal antibody recognizes a specific antigen on the surface of cancer cells. In a more preferred embodiment, this monoclonal antibody recognizes the ErbB-2 receptor on the surface of cancer cells. One example of such a monoclonal antibody is the antibody herein designated N28 or a $F(ab)_2$ dimer or $F(ab)$ monomer thereof.

In another aspect, the present invention relates to a method for treating a disorder or disease treatable with allicin that comprises administering to an individual in need thereof a conjugate of the enzyme alliinase with a carrier protein that targets the conjugate to a desired tissue or organ in the body, followed by administering alliin, whereby allicin is generated at the tissue or organ site, where it can exert its biological activity.

Several types of cancers and infectious diseases can be treated by the method of the present invention.

DETAILED DESCRIPTION OF THE INVENTION

Figure 8:
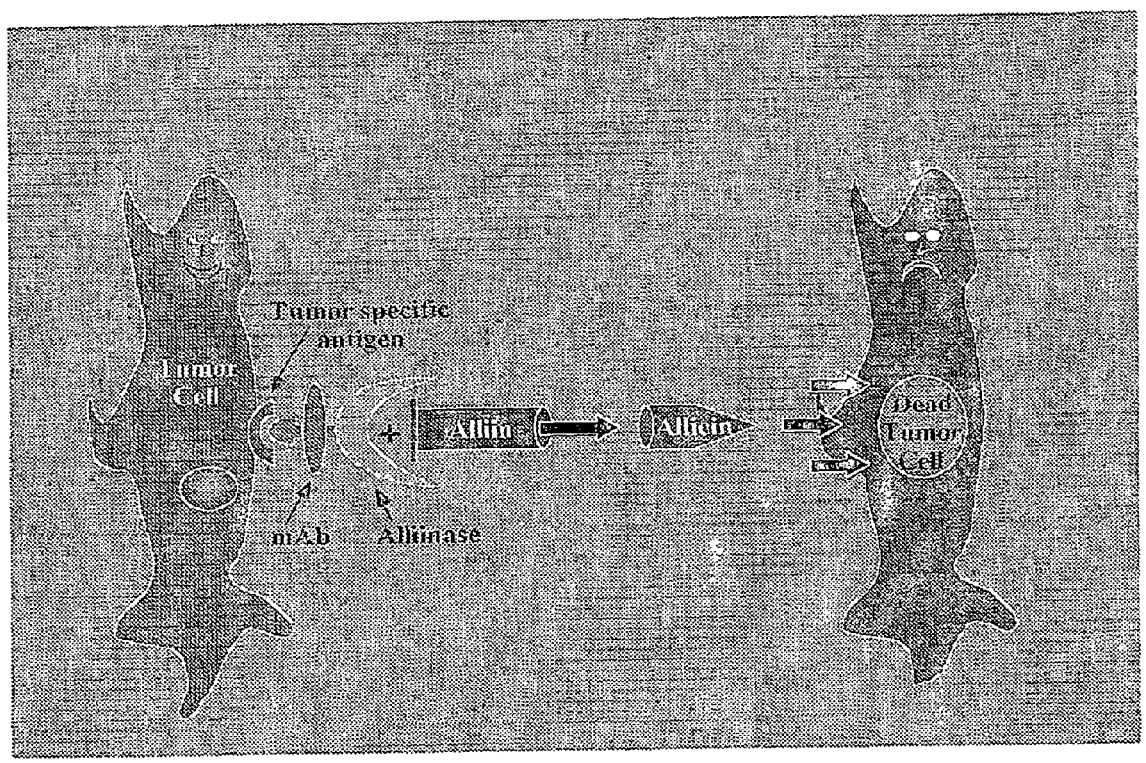
FIG. 8 depicts the concept of using mAb-alliinase conjugate together with alliin for in situ production of allicin in anticancer therapy.

According to the present invention, a new approach for treating cancer and bacterial infections is provided whereby alliinase is conjugated to a carrier protein for specific delivery and targeting of the alliinase to the surface of target cells. The cells are then exposed to alliin, at which time the alliinase converts the alliin in situ to allicin, which kills the target cells. This concept is illustrated in FIG. 8, and the results shown herein validate the efficacy of the invention.

The present invention provides a method to generate allicin in situ at a desired location in the body, wherein allicin is generated directly at the site to be treated so that the allicin does not deteriorate prior to reaching the site to be treated. The allicin-producing enzyme, alliinase, is delivered directly to the sites where allicin is desired to produce its effect. Following administration of the biologically inactive and non-toxic alliinase substrate alliin, allicin production occurs only at the place where the alliinase is located. The advantages of this approach are based on the specific features of allicin, namely, its potent biological activity, its ability to rapidly penetrate through biological membranes, its extremely short lifetime in the body as well as its low toxicity, and its conversion into non-toxic and even beneficial secondary products. Thus, according to the present invention, the biologically potent active molecule allicin is generated by the alliin-alliinase system at specific targeted sites, and thus allicin will exert its toxic effect locally.

The present invention is a new concept in targeting therapy. The present invention uses the site-directed in situ production of allicin to combat infectious disease, cancer, and other allicin-sensitive disorders.

The present invention provides the enzyme alliinase in an enzymatically active form conjugated with a targeting carrier which guides the enzyme to the cell or to the microorganism of interest in the body.

Any alliinase or enzyme which has alliinase activity, either natural or recombinant, may be used in the present invention, whether the entire molecule or a derivative or fragment thereof, as long as it retains its catalytic activity and ability to generate allicin or analogs thereof in a lyase reaction from alliin substrates or analogs thereof. While natural alliinase from garlic is the preferred enzyme for use in the present invention, alliinase from any source, including onion, Brassicaceae, Fabaceae, broccoli, and even bacteria can be used. Representative amino acid sequences for alliinase from a variety of plant sources include but are not limited to those of GenBank accession numbers S35460, S29302, S29300, S29301, BAB68045, BAB68042, AAK95663, AAK96552, AAK95661, AAK95660, AAK95659, AAK95698, AAK95657, AAK95656, NP177213, NP173746, P31757, AAG52476, AAG52348, AAG12844, AAG00599, AAF81248, AAF36437, Q01594, P31756, AAD51706, AAD51705, AAD51704, AAD51703, AAD51702, AAD51701, AAD43130, AAD32696, AAD26853, AAD21617, BAA20358, AAB32477, CAA78268, CAA78267, CAA78266, CAA63482, AAA92463, and AAA32639. According to Van Damme et al (1992), sequence analysis of alliinase cDNA clones from different Alliaceae species revealed a high degree of sequence similarity, both at the nucleotide and at the amino acid levels. However, changes in the sequences can be made as long as the alliinase activity of the protein is retained.

The holoenzyme from garlic is a glycoprotein containing 5.5% carbohydrate and consists of two identical subunits, each with a molecular mass of about 55 kDa.

Jin et al (2001) identified an essential tryptophan residue in alliinase, Trpi82, that appears to be essential for the catalytic activity of alliinase.

Manabe et al (2000) isolated a cDNA clone encoding alliinase which encoded a protein of 476 amino acid residues having a molecular weight of 54,083 Da. The deduced amino acid sequence exhibited 66-69% identities with those of reported alliinases of onion, garlic, and shallot. Manabe et al stated that lysine 280 was said to be essential for the catalytic activity of the alliinase.

The technique used by Jin et al (2001) or by Manabe et al (2000) to identify alliinase activity can be used by one skilled in the art to determine if an analog, fragment, or derivative of alliinase or a related lyase has alliinase activity that can be used to convert alliin to allicin. If an enzyme has substantially the same type of activity on alliin as alliinase from garlic, that enzyme can be used in conjugates according to the present invention. For purposes of the present invention, "substantially the same activity" means that the enzyme fragment, derivative, or analog has at least 50% of the activity of alliinase from garlic in converting alliin to allicin.

An analog of alliinase has an amino acid sequence essentially corresponding to any one of the amino acid sequences of alliinase available in GenBank disclosed above. The term "essentially corresponding to" is intended to comprehend analogs with minor changes to the sequence of the protein or polypeptide which do not affect the basic characteristics thereof, particularly insofar as its catalytic activity and ability to generate allicin or analogs thereof in a lyase reaction from alliin substrates or analogs thereof is concerned. The type of changes which are generally considered to fall within the "essentially corresponding to" language are those which would result from conventional mutagenesis techniques of the DNA encoding alliinase, resulting in a few minor modifications, and screening for the desired activity in the manner discussed above.

Preferably, the analog is a variant of a native sequence or a biologically active fragment thereof which has an amino acid sequence having at least 70% identity to a native amino acid sequence and retains the biological activity thereof. More preferably, such a sequence has at least 85% identity, at least 90% identity, or most preferably at least 95% identity to a native sequence.

Analogs in accordance with the present invention may also be determined in accordance with the following procedure. Polypeptides encoded by any nucleic acid, such as DNA or RNA, which hybridize to the complement of the native DNA or RNA under highly stringent or moderately stringent conditions, as long as that polypeptide maintains the alliinase catalytic activity of a known native sequence are also considered to be within the scope of the present invention.

The nucleotide sequence of variants of known native alliinase in question, such as, for example, naturally-occurring allelic variations and splice variants, may be determined by hybridization of a cDNA library using a probe which is based on the identified polynucleotide, under highly stringent conditions. Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm = 81.5° C. + 16.6(\log M) + 0.41(\%GC) - 0.61(\% \text{form}) - 500/L$$

and for DNA:RNA hybrids, as $$Tm = 79.8° C. + 18.5(\log M) + 0.58(\%GC) - 11.8(\%GC)^2 - 0.56(\% \text{form}) - 820/L$$

where
M, molarity of monovalent cations, 0.01-0.4 M NaCl,
% GC, percentage of G and C nucleotides in DNA, 30%-75%,
% form, percentage formamide in hybridization solution, and
L, length hybrid in base pairs.

Tm is reduced by 0.5-1.5° C. (an average of 1° C. can be used for ease of calculation) for each 1% mismatching.

The Tm may also be determined experimentally. As increasing length of the hybrid (L) in the above equations increases the Tm and enhances stability, a full-length native alliinase DNA sequence can be used as the probe.

Filter hybridization is typically carried out at 68° C. (lower temperatures are used if formamide is added to compensate for the lowering of the hybridization temperature), and at high ionic strength (e.g., 5-6×SSC), which is non-stringent, and followed by one or more washes of increasing stringency, the last one being of the ultimately desired stringency. The equations for Tm can be used to estimate the appropriate Ti for the final wash, or the Tm of the perfect duplex can be determined experimentally and Ti then adjusted accordingly.

Hybridization conditions should be chosen so as to permit allelic variations and splice variants, but avoid hybridizing to other non-alliinase genes. In general, highly stringent conditions are considered to be a Ti of 5° C. below the Tm of a perfect duplex, and a 1% divergence corresponds to a 0.5-1.5° C. reduction in Tm. Use of a Ti of 5-15° C. below, more preferably 5-10° C. below, the Tm of the double stranded form of the probe is recommended for probing a cDNA library.

As used herein, highly stringent conditions are those which are tolerant of up to about 15% sequence divergence. Without limitation, examples of highly stringent (5-15° C. below the calculated Tm of the hybrid) conditions use a wash solution of 0.1×SSC (standard saline citrate) and 0.5% SDS at the appropriate Ti below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent wash conditions described above is hybridization in a solution of 6×SSC (or 6×SSPE), 5×Denhardt's reagent, 0.5% SDS, 100 µg/ml denatured, fragmented salmon sperm DNA at an appropriate incubation temperature Ti.

"Functional derivatives" as used herein covers chemical derivatives which may be prepared from the functional groups which occur as side chains on the residues or the N- or C-terminal groups, by means known in the art, and are included in the invention as long as they remain pharmaceutically acceptable, i.e., they do not destroy the catalytic activity of the corresponding alliinase enzyme as described herein. Derivatives may have chemical moieties, such as carbohydrate or phosphate residues, provided such a fraction has the same catalytic activity and remains pharmaceutically acceptable.

Suitable derivatives may include aliphatic esters of the carboxyl of the carboxyl groups, amides of the carboxyl groups by reaction with ammonia or with primary or secondary amines, N-acyl derivatives or free amino groups of the amino acid residues formed with acyl moieties (e.g., alkanoyl or carbocyclic aroyl groups) or O-acyl derivatives of free hydroxyl group (e.g., that of seryl or threonyl residues) formed with acyl moieties. Such derivatives may also include for example, polyethylene glycol side-chains which may mask antigenic sites and extend the residence of the complex or the portions thereof in body fluids.

Non-limiting examples of such derivatives are described below.

Cysteinyl residues most commonly are reacted with alpha-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-beta-(5-imidazoyl)propionic acid, chloroacetyl phosphate, N-alkylmaleimides, 3-nitro-2-pyridyl disulfide, methyl-2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5-7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidazole and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R'), such as 1-cyclohexyl-3-[2-morpholinyl-(4-ethyl)]carbodiimide or 1-ethyl-3-(4-azonia-4,4-dimethlypentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

The term "derivatives" is intended to include only those derivatives that do not change one amino acid to another of the twenty commonly-occurring natural amino acids.

The term "salts" herein refers to both salts of carboxyl groups and to acid addition salts of amino groups of the complex of the invention or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must have substantially similar biological activity to the complex of the invention or its analogs.

The term "fragment" of the enzyme alliinase or a variant thereof is intended to cover any fragment of alliinase or an analog thereof that retains the catalytic activity and ability to generate allicin in a lyase reaction from alliin substrates. For example, fragments can be readily generated from alliinase where successive residues can be removed from either or both the N-terminus or C-terminus of alliinase, or from peptides obtained thereof by enzymatic or chemical cleavage of the polypeptide. Thus, multiple substitutions are not involved in screening for catalytically active fragments of alliinase. If the removal of one or two amino acids from one end or the other does not affect the catalytic activity after testing in the standard tests, as discussed herein, such truncated polypeptides are considered to be within the scope of the present invention. Further truncations can then be carried out until it is found where the removal of another residue destroys the catalytic activity.

The targeting carrier, in one preferred embodiment, is a monoclonal antibody of either human or animal origin. It may be a natural, recombinant or humanized antibody, or it may be a derivative thereof such as a $F(ab)_2$ dimer or F(ab) monomer, Fv or a natural or recombinant single-chain Fv. The antibody must be one that recognizes a specific receptor on the cell surface to be targeted and are not internalized. Derivatives of monoclonal antibodies are those molecules that recognize the same receptor on the cell surface as the monoclonal antibody and thus can be used interchangeably with the intact monoclonal antibody in the present invention.

It should be understood that when the term "antibodies" is used with respect to the antibody embodiments of the present invention, this is intended to include intact antibodies, such as polyclonal antibodies or monoclonal antibodies (mAbs), as well as proteolytic fragments thereof such as the Fab or F(ab')2 fragments. Furthermore, the DNA encoding the variable region of the antibody can be inserted into other antibodies to produce chimeric antibodies (see, for example, Cabilly et al, U.S. Pat. No. 4,816,567) or into T-cell receptors to produce T-cells with the same broad specificity (see Eshhar et al, 1990 and Gross et al, 1989). Single-chain antibodies can also be produced and used. Single-chain antibodies can be single-chain composite polypeptides having antigen binding capabilities and comprising a pair of amino acid sequences homologous or analogous to the variable regions of an immunoglobulin light and heavy chain (linked VH-VL or single-chain FV). Both VH and VL may copy natural monoclonal antibody sequences or one or both of the chains may comprise a CDR-FR construct of the type described in Huston et al, U.S. Pat. No. 5,091,513 (the entire content of which is hereby incorporated herein by reference). The separate polypeptides analogous to the variable regions of the light and heavy chains are held together by a polypeptide linker. Methods of production of such single-chain antibodies, particularly where the DNA encoding the polypeptide structures of the VH and VL chains are known, may be accomplished in accordance with the methods described in, for example, Ladner et al, U.S. Pat. Nos. 4,946,778 and 5,096,815; and Huston et al, U.S. Pat. No. 5,091,513, the entire contents of each of which are hereby incorporated herein by reference.

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

Polyclonal antibodies are heterogeneous populations of antibody molecules derived from the sera of animals immunized with an antigen.

Monoclonal antibodies (mAbs) are a substantially homogeneous population of antibodies to specific antigens. MAbs may be obtained by methods known to those skilled in the art. See, for example Kohler et al, (1975); David et al, U.S. Pat. No. 4,376,110; Harlow et al, (1988); and Colligan et al, (2001), the entire contents of which references are incorporated entirely herein by reference. Such antibodies may be of any immunoglobulin class including IgG, IgM, IgE, IgA, and any subclass thereof. The hybridoma producing the mAbs of this invention may be cultivated in vitro or in vivo. High titers of mAbs can be obtained by in vivo production where cells from the individual hybridomas are injected intraperitoneally into pristane-primed Balb/c mice to produce ascites fluid containing high concentrations of the desired mabs. MAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Chimeric antibodies are primarily used to reduce immunogenicity during application and to increase yields in production, for example, where murine mAbs have higher yields from hybridomas but higher immunogenicity in humans, such that human/murine chimeric or humanized mAbs are used. Chimeric and humanized antibodies and methods for their production are well-known in the art, such as Cabilly et al (1984); Morrison et al (1984); Boulianne et al (1984); Cabilly et al, European Patent 0 125 023 (1984); Neuberger et al (1985); Taniguchi et al, European patent no. EP 0 171 496 (1985); Morrison et al, European patent no. EP 0 173 494 (1986); Neuberger et al, international publication WO 86/01533 (1986); Kudo et al, European patent no. EP 0 184 187 (1985); Sahagan et al (1986); Robinson et al, international publication WO 87/02671 (1987); Liu et al (1987); Sun et al (1987); Better et al (1988); and Harlow et al (1988). These references are hereby incorporated herein by reference.

A "molecule which includes the antigen-binding portion of an antibody," is intended to include not only intact immunoglobulin molecules of any isotype and generated by any animal cell line or microorganism, or generated in vitro, such as by phage display technology for constructing recombinant antibodies, but also the antigen-binding reactive fraction thereof (also referred to herein as a derivative thereof), including, but not limited to, the Fab fragment, the Fab' fragment, the $F(ab')_2$ fragment, the variable portion of the heavy and/or light chains thereof, and chimeric or single-chain antibodies incorporating such reactive fraction, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

In other embodiments of the present invention, the targeting carrier is a lectin, a carbohydrate-binding protein, a hormone, or a ligand which has specific receptor binding properties for specific cells, or a special polymer with tropism to particular tissues and cells.

Examples of monoclonal antibodies that can be coupled to alliinase for use in the present invention include, without being limited to, human or humanized monoclonal antibodies, some of which are commercially available, against a variety of specific antigens on the surfaces of cancer cells and metastatic cells. Examples of such anticancer monoclonal antibodies are the monoclonal antibodies against the ErbB-2 receptor present on the surface of many cancer cells, particularly the antibodies described in Bacus, U.S. Pat. No. 5,514,554; and Sela et al, European patent no. EP 0 554 441, which are herein incorporated by reference in their entirety. Of particular interest is the monoclonal antibody against ErbB-2 receptor herein designated N28, which was deposited at the CNCM, Institut Pasteur, Paris, France, August 1992, under the Accession Number I-1261.

Other antibodies that can be coupled to alliinase for cancer therapy according to the present invention include monoclonal antibodies against a variety of cancer cells and metastatic antigens related to, for example, breast, colorectal, prostate, or bladder cancers, and of different leukemias such as the antibodies against the CD-20 receptor containing B-lymphocytic or lymphoblastic leukemia cells. Examples of particular cancer-specific antibodies which may be used in the present invention are listed in the "e-book"*Monoclonal Antibody Index, Vol 1: Cancer* (2000).

Many patents are directed to the targeted delivery of various agents to specific cell types, such as tumor cells, bacteria, etc., using appropriate antibodies or other ligands for the targeting. Among these are the following patents, all of which are hereby incorporated herein by reference in their entireties: Greenfield et al, U.S. Pat. No. 5,122,378 (note particularly col. 10, line 36-col. 11, line 36); Bagshawe, U.S. Pat. No. 6,299,876 (note particularly col. 5, line 5-col. 6, line 15); Kaneko et al, U.S. Pat. No. 5,137,877 (note particularly col. 10, line 55-col. 11, line 60); Epstein et al, U.S. Pat. No. 6,008,319 (note particularly col. 6, lines 53-64); George et al, U.S. Pat. No. 5,861,156; Thorpe et al, U.S. Pat. No. 6,312,694; Griffiths et al, U.S. Pat. No. 5,964,131; Fitzgerald et al, U.S. Pat. No. 5,863,745; Fell, Jr. et al, U.S. Pat. No. 5,645,835; Iwasa et al, international publication no. WO 91/09134; Senter et al, European patent no. EP 0 302 473; Chang et al, European-patent EP 0 506 124. Any of the antibodies or other targeting molecules disclosed in any of these patents may be used in the course of practicing the present invention, as may the techniques of making the complexes which are disclosed therein.

This same principle can be used to damage any other types of pathogenic cells or offending pathogens. The only requirement is the availability of highly specific monoclonal antibodies to the target cells or pathogen which can be coupled to alliinase. Thus, the targeting carrier may be a monoclonal antibody against an infectious disease. Many such antibodies currently exist against a variety of infectious agents such as viruses, e.g., hepatitis B and C, HIV, CMV, etc., as well as against other infectious diseases such as tuberculosis, lung inflammation. (bacterial, viral or fungal), bronchitis (viral or bacterial), leprosy, meningitis (viral, bacterial, or fungal), plague, typhus or paratyphus A and B, influenza, herpes zoster, cholera, malaria, measles, acute and chronic liver infections (including from hepatitis B and C), rabies, and AIDS. Some such examples are monoclonal antibodies against hepatitis viruses or other viruses such as HIV, against fungi such as *Candida albicans*, against bacterial infections such as Staphylococci or Streptococci causing bateriemia, against parasites which appear in the circulation such as *Trypanosomes, Plasmodium, Leishmania*, and the like.

Many of these monoclonal antibodies are commercially available, such as from Research Diagnostics, Inc., of Flanders, NJ. Alternatively, a monoclonal antibody specific for a given pathogen or disease can be selected from among those listed in the "e-book" *Monoclonal Antibody Index, Vol. 2: Transplant, Infection and Heart*, (2001).

Alliinase can be attached to a targeting carrier by chemical means by generating covalently bound conjugates, as well as by physical means such as by affinity binding, entrapping the enzyme within a polymer matrix or membrane (liposome), or microencapsulating the enzyme within semipermeable polymer membranes.

Any suitable technique used to prepare conjugates for biotechnological or medical applications can be used for the present invention. One example is the technique described in Miron et al (international publication WO 97/39115) Other chemical conjugation methods are described in Epstein et al, U.S. Pat. No. 6,008,319 (note particularly col. 7, lines 22-60). The entire contents of both of these patents are hereby incorporated herein by reference. The alliinase can be bound to the carrier directly or through a spacer.

The carriers used in the present invention are antibodies or other ligands which recognize cell receptors, as well as specific polymers, liposomes, etc. Coupling alliinase to these carriers involves mild reactions between amino acid residues of the enzyme and functional groups of the carrier. Functional groups of carriers that can be used in the present invention are thiol, hydroxyl, amino, and carboxyl groups, which must be activated for coupling with alliinase. Coupling can be effected by various chemical crosslinking methods, forming peptide (amide), azo, thioether, disulfide, and other bonds. Any of these methods can be used for this invention. For example, to form a peptide bond, carboxyl groups of the carrier are converted to reactive derivatives such as N-hydroxysuccinimide ester. And these derivatives form peptide bonds with free amino groups of alliinase. It is also possible to form peptide bonds between free carboxyl or amino groups of the enzyme, and amino groups or carboxyl groups of the carrier, respectively, using condensing agents such as cabodiimides and Woodward's reagent K.

Another possibility is to use a molecule which serves as a spacer, e.g., epsilon-aminocaproic acid or 3-(2-pyridyldithio) propionic acid N-hydroxysuccinimide ester (SPDP). The spacer is first attached either to the carrier or to alliinase through an amino group. Then, using the methods described above, the two entities are combined.

For stabilization or for immunological reasons, alliinase can be coupled with various biocompatible synthetic polymers such as methoxypolyethylene glycol (mPEG) prior to being coupled to the carrier molecule. Pegylation of alliinase is carried out by standard techniques, well known to one skilled in the art.

Alliinase can be coupled with the targeting carrier using, for example, biotinlyated alliinase or haptenized alliinase that can interact with avidin on the antibody.

Another approach for preparing conjugates of the present invention consists in developing recombinant carrier-alliinase fusion proteins, for example, mAb-alliinase, consisting of single molecular entities. Genetically engineered fusion proteins may be constructed by cloning the gene sequences of antibody light chains and heavy chains fused to sequences encoding alliinase. As an example, mRNA from hybridoma cells expressing a monoclonal antibody is isolated. From this mRNA, cDNA is reverse transcribed and amplified by polymerase chain reaction. Specific regions encoding heavy and light chains of an immunoglobulin, e.g., variable and/or constant regions, can be amplified by the selection of appropriate oligonucleotide primers targeting the desired region(s). The cDNA is sequenced, mapped by restriction endonucleases, and cloned into an appropriate transfer vector. At a minimum, the immunoglobulin sequences encoding an antigen binding domain, i.e., the variable light chain and variable heavy chain regions, are contained in the transfer vector. In addition, a truncated or full-length portion of the constant region encoding the original or another immunoglobin can be joined in frame with the variable region, to allow expression of the joined regions. For example, a preferred embodiment of the invention encodes a chimeric mAb, comprised of murine variable regions linked to their corresponding human constant regions of the heavy and light chains.

An appropriate DNA sequence, encoding at least one alliinase peptide, is then ligated proximate to a region of an immunoglobulin gene encoding the carboxy-terminus, preferably a constant region, most preferably the constant region of a heavy chain. The best site for attachment for each alliinase may be different and may be easily determined via experimental methods. For example, none or various lengths of amino acid encoding linkers may be inserted between the alliinase and the carboxy-terminus of the immunoglobulin gene. The resulting expression products can then be tested for biologic activity.

The completed engineered gene for the fusion protein is inserted into an expression vector, which can be introduced into eukaryotic or prokaryotic cells by gene transfection methods, e.g., electroporation or the calcium phosphate method. The fusion protein product can then be expressed in large-scale cell culture and purified.

The C-terminal end of alliinase, or any biologically active analog or fragment thereof, may be fused to the N-terminal end of an immunoglobulin chain, preferably a single-chain antibody (scFv) or an antigen-binding fragment thereof. The reverse constructs can also be prepared, where the C-terminal end of the antibody chain is fused to the N-terminal end of the alliinase molecule. In order to engineer an alliinase/antibody fusion protein that allows the active complex to be maintained, a flexible peptide linker, for example Gly-Gly-Gly-Gly-Ser (GGGGS) (SEQ ID NO:1) repeats, may be employed. Preferably these linkers are up to about 30 amino acids in length.

The present invention also concerns DNA sequences encoding the above fusion protein of the invention, as well as DNA vectors carrying such DNA sequences for expression in suitable prokaryotic or eukaryotic host cells. The ability to generate large quantities of heterologous proteins using a recombinant protein expression system has led to the development of various therapeutic agents. The various expression hosts from which recombinant proteins can be generated range from prokaryotic in origin (e.g., bacteria), through lower eukaryotes (e.g., yeast) to higher eukaryotic species (e.g., insect and mammalian cells). All of these systems rely upon the same principle, i.e., introducing the DNA sequence of the protein of interest into the chosen cell type (in a transient or stable fashion, as an integrated or episomal element)

and using the host transcription, translation and transportation machinery to over-express the introduced DNA sequence as a heterologous protein.

Other techniques for making fusion proteins, and particularly with antibodies, are disclosed in the patents listed and incorporated by reference hereinabove.

The present invention provides a pharmaceutical composition comprising a conjugate of the invention and a pharmaceutically acceptable carrier. While any suitable formulation of the composition is encompassed by the invention, preferably, it will be adapted for intravenous administration.

Pharmaceutical compositions according to the present invention can be administered by any convenient route, including parenteral, subcutaneous, intravenous, intramuscular, intraperitoneal, or transdermal. Alternatively or concomitantly, administration may be by the oral route. The dosage administered depends upon the age, health, and weight of the recipient, nature of concurrent treatment, if any, and the nature of the effect desired.

Compositions within the scope of the present invention include all compositions wherein the conjugate is contained in an amount effective to achieve its intended purpose. While individual needs vary, determination of optimal ranges of effective amounts of each compound is within the skill of the art. As the conjugate is non-toxic and, unless it binds to its target cell, is removed quickly from the system, there is, practically, no maximum dosage amount. Typical preferred dosages comprise 0.01 to 100 mg/kg body weight. The preferred dosages comprising 0.1 to 100 mg/kg body weight. The most preferred dosages comprise 1 to 50 mg/kg body weight.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations contain from about 0.01 to about 99 percent by weight, preferably from about 20 to 75 percent by weight, active compound(s), together with the excipient. For purposes of the present invention, all percentages are by weight unless otherwise indicated. In addition to the following described pharmaceutical composition, the compounds of the present invention can be formulated as inclusion complexes, such as cyclodextrin inclusion complexes.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular active ingredient, as well as by the particular method used to administer the composition. Accordingly, there is a wide variety of suitable formulations of the pharmaceutical compositions of the present invention. While the preferred route for administering the conjugates of the present invention is oral, formulations can also be prepared for aerosol, parenteral, subcutaneous, intravenous, intraarterial, intramuscular, intraperitoneal, intratracheal, rectal, and vaginal administration.

Suitable formulations for parenteral administration include aqueous solutions of the active compounds in water-soluble form, such as water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, including, for example, sodium carboxymethyl cellulose, sorbitol, and/or dextran. Optionally, the suspension may also contain stabilizers.

Other pharmaceutically acceptable carriers for the active ingredients according to the present invention are liposomes, pharmaceutical compositions in which the active ingredient is contained either dispersed or variously present in corpuscles contained either dispersed or variously present in corpuscles consisting of aqueous concentric layers adherent to lipid layers. The active ingredient may be present both in the aqueous layer and in the lipidic layer, inside or outside, or, in any event, in the non-homogeneous system generally known as a liposomic suspension.

The hydrophobic layer, or lipid layer, generally, but not exclusively, comprises phospholipids such as lecithin and sphingomyelin, steroids such as cholesterol, more or less ionic surface active substances such as dicetyl phosphate, stearylamine, or phosphatidic acid, and/or other materials of a hydrophobic nature.

Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents. Capsule forms can be of the ordinary hard-or soft-shelled gelatin type containing, for example, surfactants, lubricant, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscaramellose sodium, talc, magnesium stearate, calcium stearate, zinc stearate, stearic acid, and other preservatives, flavoring agents, and pharmaceutically acceptable disintegrating agents, moistening agents preservatives flavoring agents, and pharmacologically compatible carriers. Lozenge forms can comprise the active ingredient in a carrier, usually sucrose and acacia or tragacanth, as well as pastilles comprising the active ingredient in an inert base such as gelatin or glycerin, or sucrose and acacia. Emulsions and the like can contain, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds can be administered in a physiologically acceptable diluent in a pharmaceutical carrier, such as a sterile liquid or mixture of liquids, including water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene glycol) 400, oils, fatty acids, fatty acid esters or glycerides, or acetylated fatty acid glycerides, with or without the addition of a pharmaceutically acceptable surfactant, such as soap or a detergent, suspending agent, such as carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Fatty acids can be used in parenteral formulations, including oleic acid, stearic acid, and isostearic acid. Ethyl oleate and isopropyl myristate are examples of suitable fatty acid esters. Suitable salts for use in parenteral formulations include fatty alkali metal, ammonium, and triethanolamine salts, and suitable detergents include cationic detergents such as dimethyl dialkyl ammonium halides, and alkyl pyridimium halides; anionic detergents such as dimethyl olefin sulfonates, alkyl, olefin, ether, and monoglyceride sulfates and sulfosuccinates; polyoxyethylenepolypropylene copolymers; amphoteric detergents such as alkyl-β-aminopropionates and 2-alkyl-imidazoline quaternary ammonium salts; and mixtures thereof.

Parenteral formulations typically contain from about 0.5 to 25% by weight of the conjugate in solution or suspension. Suitable preservatives and buffers can be used in these formulations. In order to minimize of eliminate irritation at the site of injection, these compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be present in unit dose or multiple dose sealed containers, such as ampoules and vials, and can be stored in a freeze-dried (lyophilized) condition requiring only the addition of the sterile liquid carrier, e.g., water, for injections immediately prior to use. Extemporaneous injection solutions and suspensions can be prepared from sterile powders, granules, and tablets of the kind previously described.

Any number of assays well known in the art may be used to test whether a particular conjugate is sufficiently enzymatically active to convert alliin or a derivative thereof to allicin, and if this conjugate can successfully be directed to the desired site in vivo.

In determining the dosages of the conjugate and alliin to-be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ID_{50}$ level of the active ingredient in question can be one of the dosage levels selected, and the other two selected to reach a toxic level. The lowest dose is that which does not-exhibit a biologically demonstrable effect. The toxicology tests should be repeated using appropriate new doses calculated on the basis of the results obtained. Young, healthy mice or rats belonging to a well-defined strain are the first choice of species, and the first studies generally use the preferred route of administration. Control groups given a placebo or which are untreated are included in the tests. Tests for general toxicity, as outlined above, should normally be repeated in another non-rodent species, e.g., a rabbit or dog. Studies may also be repeated using alternate routes of administration.

Single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds. Data on single dose toxicity, e.g., $ID_{50}$, the dosage at which halr of the experimental animals die, is to be expressed in units of weight or volume per kg of body weight and should generally be furnished for at least two species with different modes of administration. In addition to the $ID_{50}$ value in rodents, it is desirable to determine the highest tolerated dose and/or lowest lethal dose for other species, i.e., dog and rabbit.

Pharmacological animal studies on pharmacokinetics revealing, e.g., absorption, distribution, biotransformation, and excretion of the active ingredient and metabolites are then performed. Using the results obtained, studies on human pharmacology are then designed. Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and alliin are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compositions of the present invention are then ready for clinical trials to compare the efficacy of the conjugates to existing therapy. A dose-response relationship to therapeutic effect and for side effects can be more finely established at this point.

The amount of conjugate of the present invention and of alliin to be administered to any given patient must be determined empirically, and will differ depending upon the condition of the patients. Relatively small amounts of the active ingredients can be administered at first, with steadily increasing dosages if no adverse effects are noted. Of course, the maximum safe toxicity dosage as determined should not be exceeded.

The present invention further provides a kit comprising in separate compartments a pharmaceutical composition containing the conjugate and an optional pharmaceutically acceptable carrier as described above, and a pharmaceutical composition containing alliin in an optional pharmaceutically acceptable carrier. The kit also preferably contains instructions for administering the two compositions, including the dosage and the timing of administration of the two principles. The alliin is preferably formulated for administration per os, intraparentally, or intravenously.

The present invention also provides a method for treating a disorder or disease which is treatable with allicin that comprises administering to an individual in need thereof a conjugate of the enzyme alliinase with a targeting carrier that targets the conjugate to a desired tissue or organ in the body, followed by administration alliin. In this way, allicin is generated at the desired tissue or organ, thus exerting its biological activity. When the targeting carrier is related to a cancer antigen, the method is suitable for treatment of cancer. When the targeting carrier is related to an antigen typical of an infectious disease, the method is suitable for treating the infectious disease.

In treating a disorder or disease treatable with allicin, the conjugate of the targeting carrier is administered first, followed by administration of alliin. Preferably, the alliin is administered from about 30 minutes to up about five hours after administration of the conjugate. The administration of alliin may be repeated one or several times as necessary, in intervals to be decided according to the stage of the disease and condition of the patient.

Administration of alliin, which is a non-toxic amino acid derivative, essentially potentiates the carrier-alliinase conjugate located on the target cell. The enzymatic activity of alliinase in the conjugate enables continuous generation of allicin at the target cell site. Generation of allicin depends on the availability of the substrate alliin. Since mammalian cells do not produce a lyase type of enzyme such as alliinase, the administration of alliin per os or intravenously or intraperitoneally poses no toxic danger, as the alliin is converted to allicin only by the alliinase which is ligated to the carrier.

Since cells treated only with alliin (in the absence of the conjugate) or only with the conjugate (without the addition of alliin) were not inhibited in their growth, the conjugates of the present invention clearly have a very wide range of potential applications.

The invention will now be illustrated by the following non-limiting examples:

EXAMPLES

Material and Methods

Materials

Alliinase was purified from garlic cloves. 3-(2-Pyridyldithio)propionic acid N-hydroxysuccinimide ester (SPDP) was obtained from Pharmacia Fine Chemicals (Uppsala, Sweden) and dithiothreitol (DTT) from Sigma (St. Louis, Mo., USA). Alliin was synthesized from L-cysteine and allyl bromide after oxidation by $H_2O_2$ according to Stoll et al (1951). 2-Nitro-5-thiobenzoate (NTB) was synthesized according to Degani et al (1971). Monomethoxypolyethylene glycol (2000 and 5000) were from Aldrich (Milwaukee, Wis., USA). N-hydroxy succinimide derivates of monomethoxypolyethylene glycol were prepared according to Miron et al (1993).

Biochemical Analysis

Protein concentration was measured at 280 nm, using $E_{280}$=77,000 $M^{-1}$ $cm^{-1}$ for alliinase and 210,000 $M^{-1}$ $cm^{-1}$ for purified monoclonal antibody (mAb). The concentration of SPDP in SPDP-modified proteins was determined after gel-filtration (Sephadex G-50) in presence of 5 mM DTT using $E_{340}$=8100 (Carlsson et al, 1978).

Purification of alliinase was done as described by Rabinkov et al (1995).

Alliinase activity was measured according to Miron et al (1998) using alliin substrate in presence of 2-nitro-5-thiobenzoate (NTB). Determination of alliinase activity was carried out in a 96-well plate, using alliin (10 μg/well) and NTB ($3 \times 10^{-4}$ M) in 50 mM phosphate buffer pH 7.2 containing 2 mM EDTA. The decrease in the absorbance at 412 nm was recorded 30 min later (room temperature).

Activity assay of the alliinase-antibody conjugates was done by NTB methods either in cell free system (kinetics) or by ELISA, after adsorbing the conjugate to wells pre-coated with either anti-mouse antibodies or cells containing the antigen to the antibody. Binding of mAb-alliinase either to wells precoated with goat anti-mouse antibodies or to cell receptors (pre-fixed sub-confluent cells of N87 or CB-2 cells with 3% paraformaldehyde in PBS in 96-well plates) was done at room temperature for 1-2 hours. Unbound proteins were removed by washing (×3) with PBST (PBS containing 0.1% Tween 20). Assay of alliinase activity of the bound conjugate was done in presence of NTB and alliin as described above.

Chemical Modification of Protein with SPDP

SPDP (5-10 mM in DMSO) aliquots were added at room temperature to alliinase solution in phosphate buffer pH 6.5, for 1 hour. Removal of excess of SPDP was done by gel filtration onto SEPHADEX G-50 equilibrated with 10% glycerol in 50 mM phosphate buffer pH 6.5. The protein peak was collected and concentrated by CENTRIPREP-30 (cut off 30 kDa; Amicon, Beverly, Mass., USA) at 4° C.

Pegylation of alliinase was performed by adding various amounts of succinimidyl carbonate polyethyleneglycol (SC-PEG) to the gel-filtered SPDP-alliinase in glycerol (10-50%) in 50 mM phosphate buffer pH 6.5. The modification mixtures were stored at 4° C. overnight, then gel-filtered on SUPERDEX 200 (XK 16×70 cm) column, equilibrated with PBS, flow rate 1 ml/min. Determination of polyethylene glycol attached to alliinase was done according to Nag et al (1996).

Antibodies mAb #N28.6 to ErbB-2 (Hurwitz et al (1995), kindly provided by Dr. E. Hurwitz, Dept of Immunology, The Weizmann Intitute of Science, Rehovoth, Israel, was partially purified from ascites fluid by using caprylic acid as described before (McKinney et al, 1987) or affinity chromatography on immobilized-protein A or protein L.

Polyclonal antibodies (goat anti-mouse) were purified from sera by using ammonium sulfate precipitation.

F(ab)$_2$ dimers were prepared from #N28.6 mAb 28.6 in 0.1M citrate-phosphate buffer, pH 3.7, by pepsin digestion (1 mg pepsin/15 mg antibodies) for 4 hours at 37° C. Isolation of F(ab)$_2$ dimers was done by gel filtration (1 ml/min) onto SUPERDEX-200 column (XK 16×70) pre-equilibrated with PBS.

Cell Line and Tissue Culture

The following cell lines were used: N87 human gastric tumor cell line expressing the ErbB-2 receptors (described by Park et al, 1990); CB-2 cell line, generated by transfection of Chinese hamster ovary (CHO) cells with mammalian expression vectors that direct expression of ErbB-2 (Tzahar et al, 1996); and 32D cell line known to be devoid of the ErbB-2 receptors (described by Pinkas-Kramarski, 1996).

Cells expressing ErbB-2 (CB-2) were grown in DMEM/F12(1:1) medium supplemented with antibiotics and 10% heat-inactivated BCS (bovine calf serum). N87 cells were grown in DMEM medium supplemented with antibiotics and 10% heat-inactivated FCS (fetal calf serum). 32D cells were grown in suspension in RMPI 1640 medium supplemented with glutamine, antibiotics, IL-3 and 10% FCS.

The cell lines CB-2, N87 and 32D were kindly obtained from Prof. Y. Yarden and normal human foreskin fibroblasts were kindly obtained from Prof. B. Geiger, both from the Weizmann Institute.

Cell Proliferation Assay

[Methyl-$^3$H]thymidine incorporation (Amersham Pharmacia Biotech, UK) into DNA was measured in 96-well plates. Cells (1,000-20,000 cells/well) were grown 6 h after seeding at 37° C. Cells were treated with conjugates for 1 hour and then 3×washed with medium. Medium (serum supplemented) ±alliin was added, as well as 0.6-0.8 μCi [methyl-$^3$H] thymidine. Cells were harvested after 16 hours incubation at 37° C.

Viability of living cells was done after staining with Trypan Blue (0.025%) for 10 minutes.

Determination of Allicin and Alliin

Quantitative determinations of alliin and allicin were obtained using a LKB HPLC system with a SP 4290 integrator (Spectra-Physics). The separation was achieved on a LiChrosorb RP-18 (7 mm) column, using methanol (60%) in water containing 0.05% trifluoroacetic acid as eluant.

In Vitro Experiments with mAb-Alliinase Conjugates

Example 1

Preparation of Conjugates of Alliinase with mAb to ErbB-2 Receptor

A stable conjugate was prepared by chemically coupling purified garlic alliinase with purified mAb to the ErbB-2 receptor N28 IgG1 (Stancovski et al, 1991). In some preparations the SPDP-aliinase was reacted with polyethylene glycol, either mPEG2000 or mPEG5000, to minimize its antigenicity (Kamisaki et al, 1981). The enzymatic activity of the mAb-alliinase conjugate and its ability to convert alliin to allicin was found to be comparable to that of the non-ligated alliinase preparation. The enzymatic activity of the mAb-alliinase conjugates were determined both in solution as well as by a solid-phase assay, using our previously reported chromophoric method (Miron et al, 1998).

Thus, alliinase (2 mg/ml in 25 mM HEPES 7.0 buffer, containing 50% glycerol) was reacted with SPDP (20 µl of 10 mM SPDP in DMSO/1.0 ml of alliinase solution for 30 minutes at room temperature). Excess of SPDP was removed by gel filtration (Sephadex G-50, pre-equilibrated with 50 mM phosphate buffer pH 6.5 containing 10% glycerol). The SPDP-modified alliinase (1-3 residues SPDP/enzyme) was concentrated and stored in 25 mM phosphate buffer containing 50% glycerol and stored at −20° C. or coupled immediately to the reduced form of the SPDP-modified monoclonal antibody to ErbB-2 (mAb-SH) prepared as described below.

ErbB-2 mAb (1 mg/ml) was modified with SPDP (15 µl of 10 mM SPDP in DMSO/1.0 ml of mAb, 30 minutes, room temperature), SEPHADEX G-50 gel-filtered as described above, concentrated and stored in PBS at 4° C. (5-10 SPDP/mAb).

The SPDP-mAb was reduced with DTT (5 mM) at room temperature for 10-20 minutes. Excess of DTT was removed by gel-filtration (PD-10) pre-equilibrated with 50 mM phosphate buffer pH 6.5 containing 10% glycerol. The protein containing fractions were collected and immediately combined with SPDP-alliinase, (10% excess of SPDP-alliinase over mAb-SH). The conjugation mixture was stored 1 hour at 4° C. in presence of 20% sucrose (added solid to the conjugation mixture) and concentrated by Centricon. The conjugate alliinase-mAb was separated from free alliinase by SUPERDEX 200 gel-filtration, and then stored in 25 mM phosphate buffer pH 6.5 containing 50% glycerol and 2 mM pyridoxal 5-phosphate at −20° C.

Example 2

Effect of Allicin and Alliin on Tissue Cultured Cells

Figure 1:
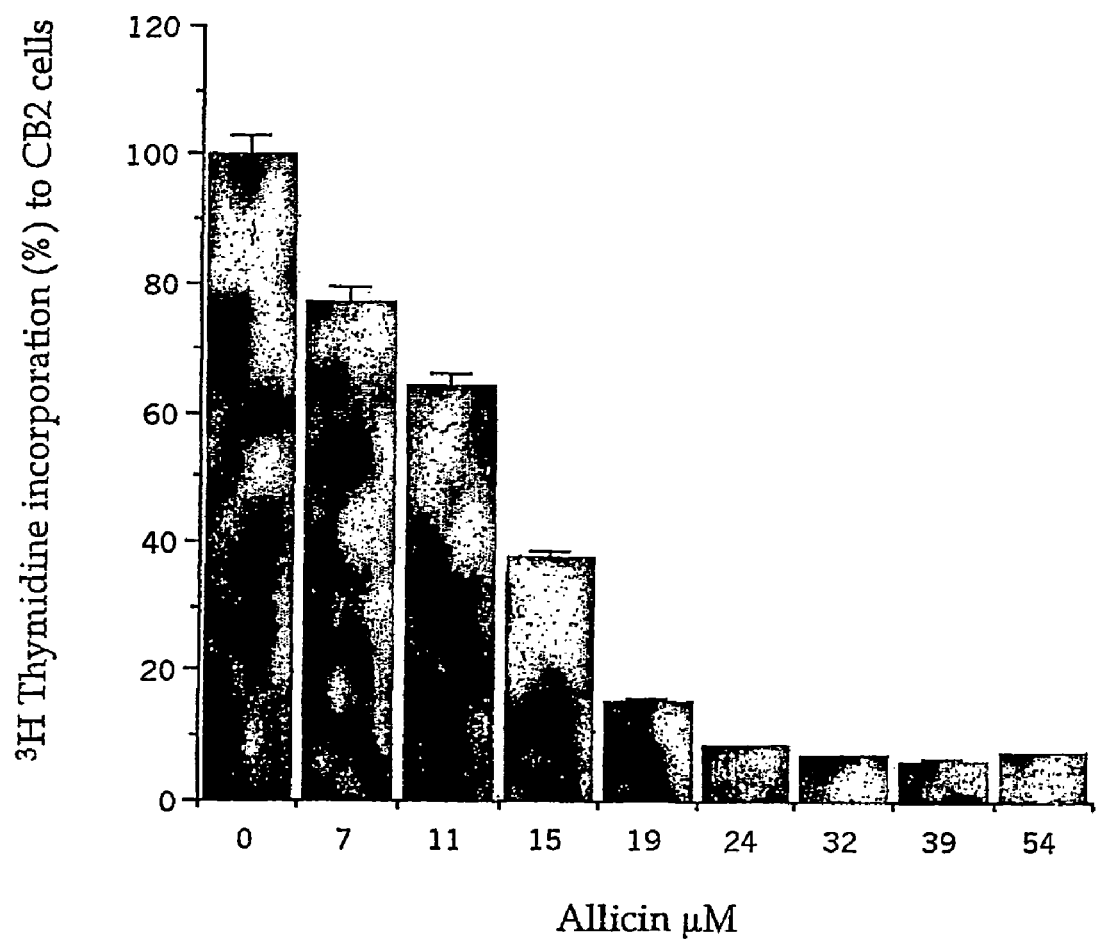
FIG. 1 shows inhibition of CB-2 cell proliferation by different concentrations of allicin.

Different concentrations of pure allicin were applied to tissue cultured human CB-2 cancer cells for quantitative determination of the effective concentration. Thus, CB-2 cells were cultured in 96-well plate (2000 cells/well) for 6-16 h at 37° C. Pure allicin was added (10 µl/well) from pre-diluted allicin solutions in PBS to final concentrations of 0-54 µM (0-9 µg/ml). [$^3$H]-Thymidine diluted with medium was added to the cell culture (0.8 µCi/well). Cells were harvested after incubation for 16 h at 37° C. and the level of incorporated [$^3$H]-thymidine was measured to determine the extent of cell proliferation. The results are shown in FIG. 1. These results demonstrate that addition of different concentrations of pure allicin to cell cultures inhibits DNA synthesis.

Figure 2A:
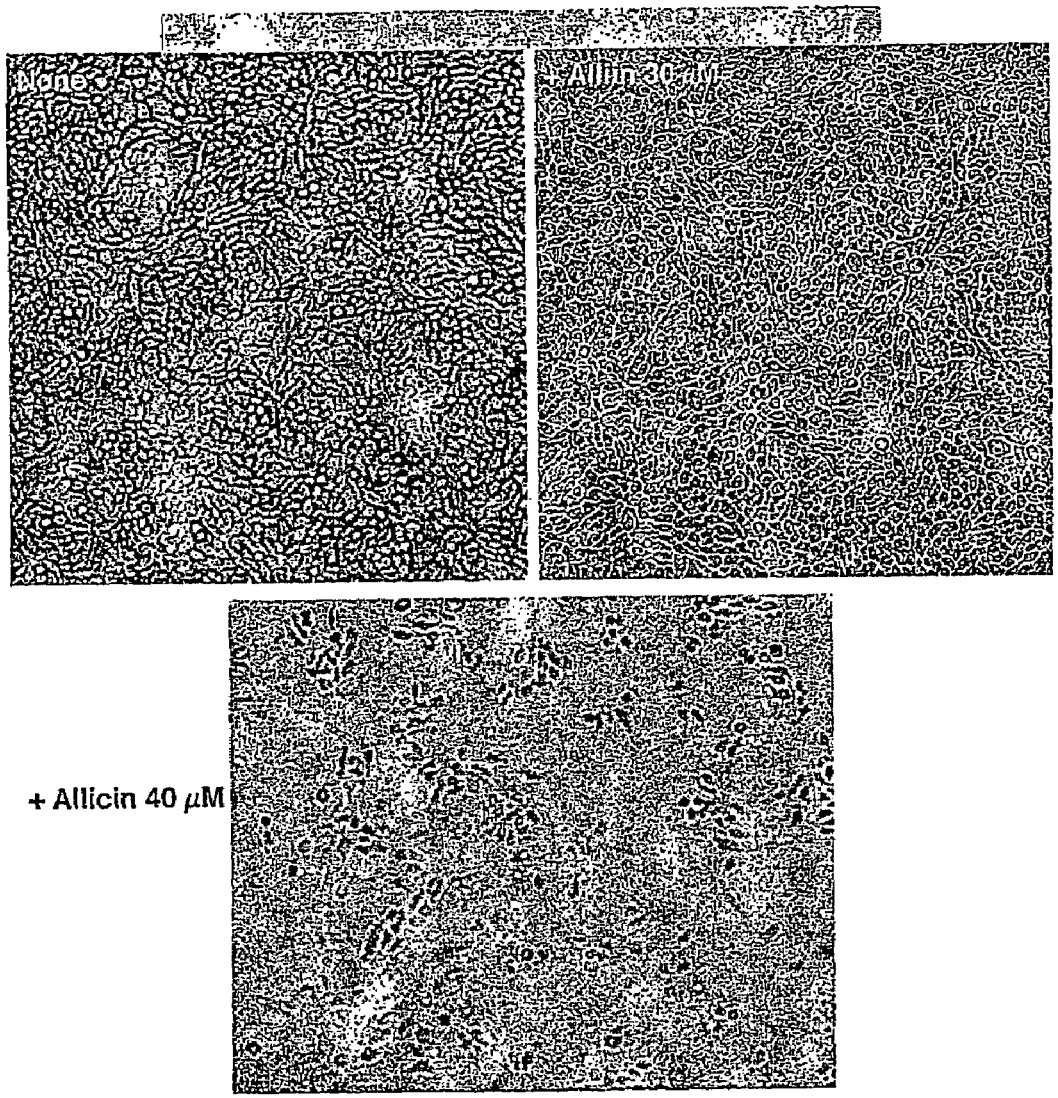
FIGS. 2A-2C show tissue cultured CB-2 cells (FIG. 2A), N87 cells (FIG. 2B), and normal human foreskin fibroblasts (FIG. 2C) stained with Trypan blue, untreated (upper left pictures) or after exposure to alliin (upper right pictures) or to allicin (lower pictures)×400.
Figure 2B:
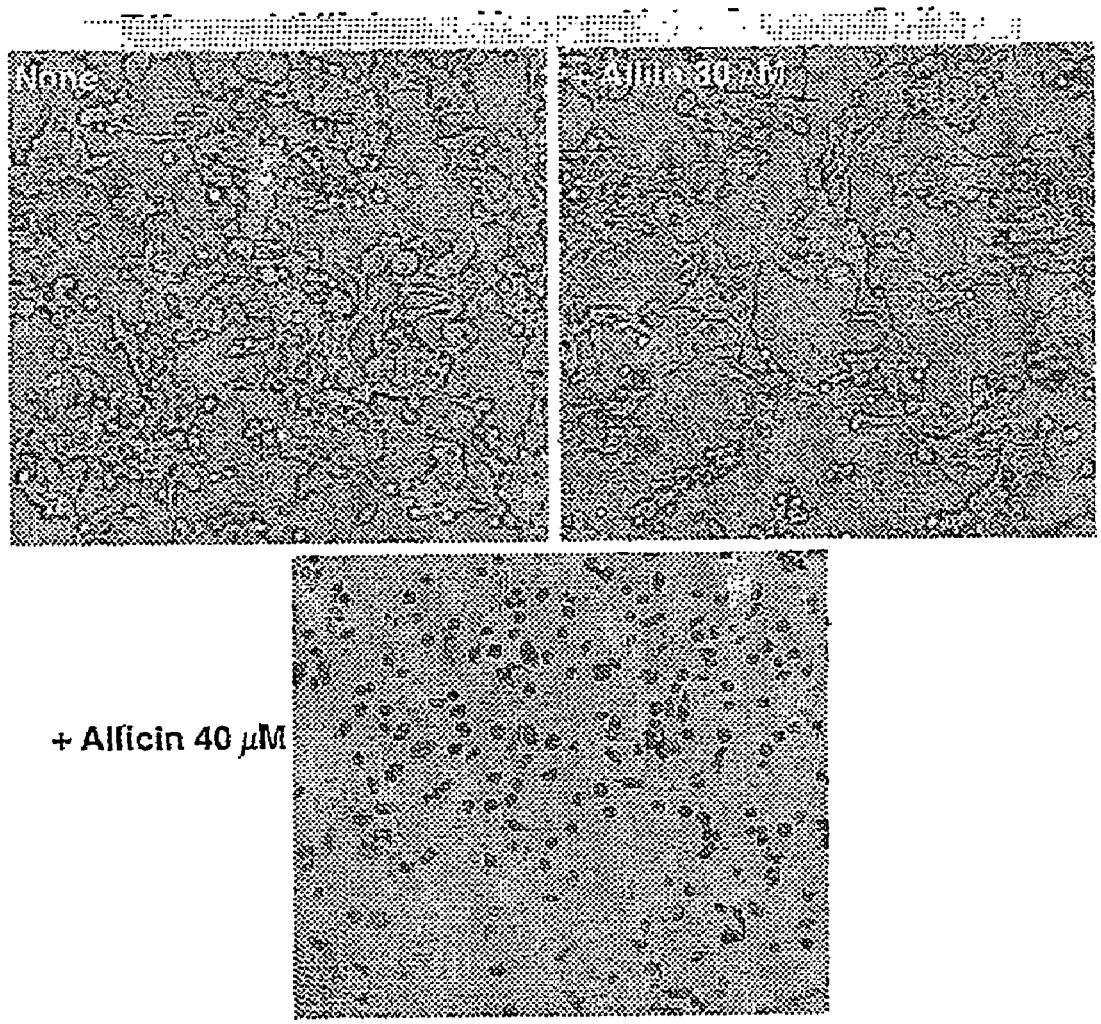
Figure 2C:
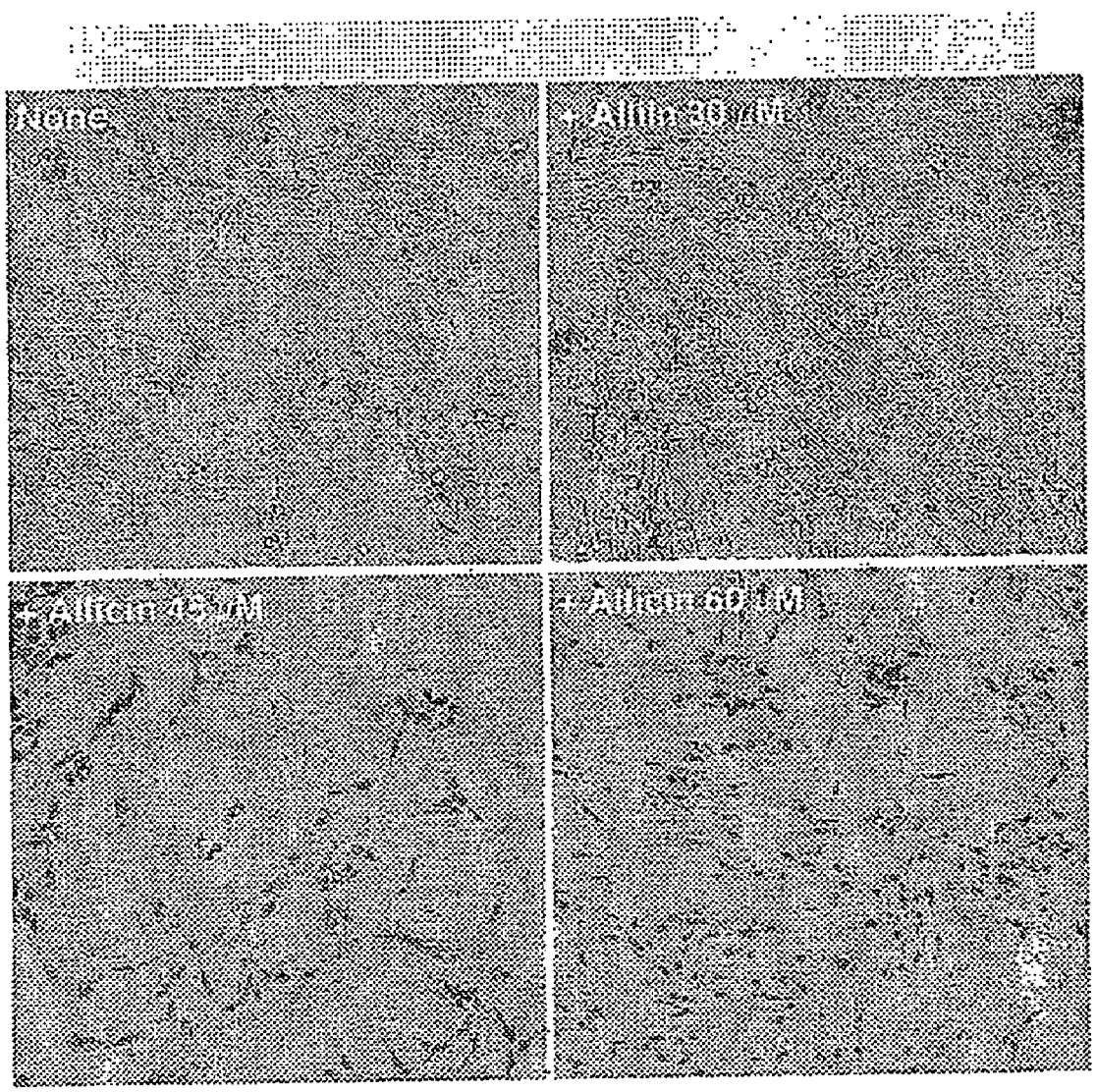

In parallel, CB-2 cells treated with alliin or allicin were stained with Trypan blue to monitor cell viability. The lethal concentration of allicin was found to be about 20 µM (FIG. 2A). A similar lethal concentration was found for N87 cancer cells (FIG. 2B) as well as for normal human foreskin fibroblasts (FIG. 2C). Alliin had no toxic effects in the above cells at concentrations of up to 200 µM.

Example 3 mAb-Alliinase Conjugates Produce Allicin after Specifically Binding to Target Cells To test whether mAb-alliinase conjugates are able to produce allicin from alliin after specifically binding to target cells, cultures of CB-2 (10,000 cells/well) and N87 cells (20,000 cells/well) grown overnight in 96-well plates were fixed with 3% paraformaldehyde (30 minutes) and washed with PBST. Fixed cells were treated with mAb to ErbB-2 receptor only or with conjugates consisting of either mAb-alliinase or F(ab)-alliinase (which was obtained after reduction of the Fc depleted antibody) (2 µg/well) for 1 h at 37° C. The wells were washed (×3) with PBST and incubated with alliin (0.1 mg/ml, 0.1 ml/well) in $4\times10^{-4}$ M NTB in 50 mM phosphate buffer pH 7.4 containing 2 mM EDTA. Controls of fixed cells with alliin/NTB were used. Readings were done by ELISA Reader after 30 minutes (A412).

Figure 3:
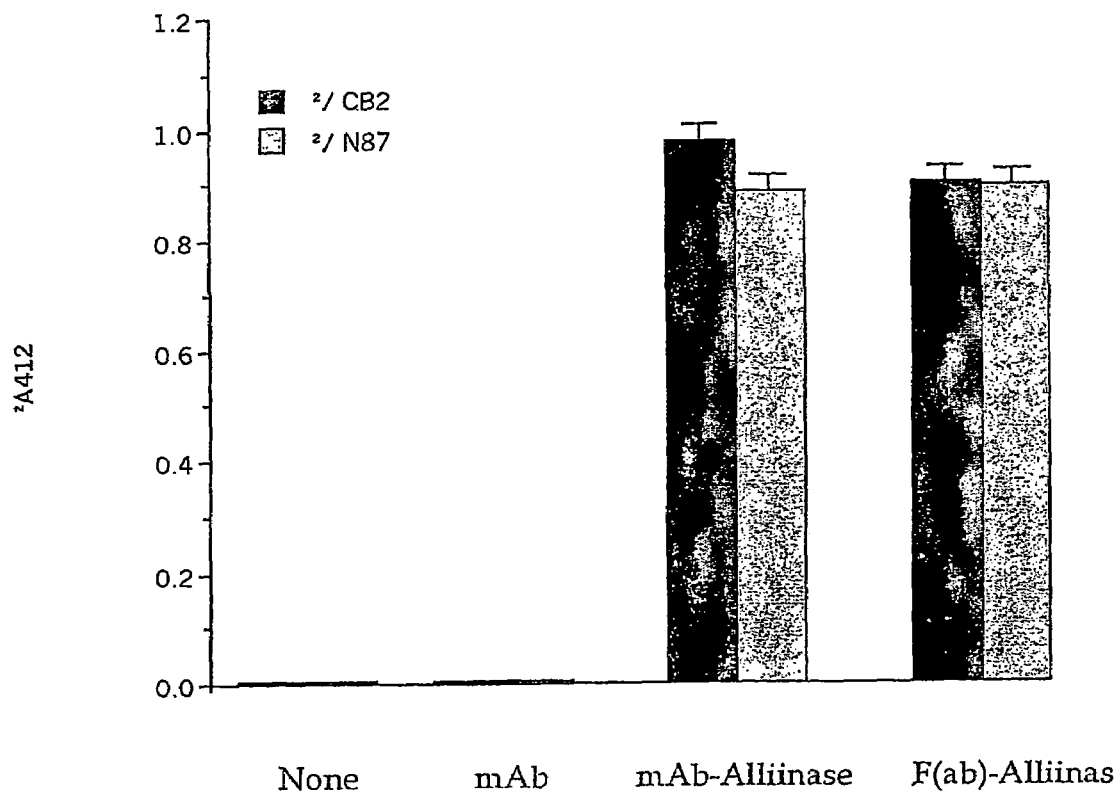
FIG. 3 shows determination of allicin produced after binding of mAB ErbB-2-alliinase conjugates or F(ab)-alliinase to CB-2 (black columns) and N87 (gray columns) cancer cells which express ErbB-2 receptors.

The results are shown in FIG. 3 wherein the black columns represent CB-2 cells and the gray columns represent N87 cells. The results show that the mAb-alliinase and F(ab)-alliinase conjugates obtained as described above retain their specificity of binding to the ErbB-2 receptors which are present on the surface of both tissue cultured cancer N87 and CB-2 cells. The bound conjugates also retained their enzymatic activity and the ability to produce allicin upon the addition of alliin was used as an assay to monitor the presence of ErbB-2 receptors on other cell lines.

Figure 4:
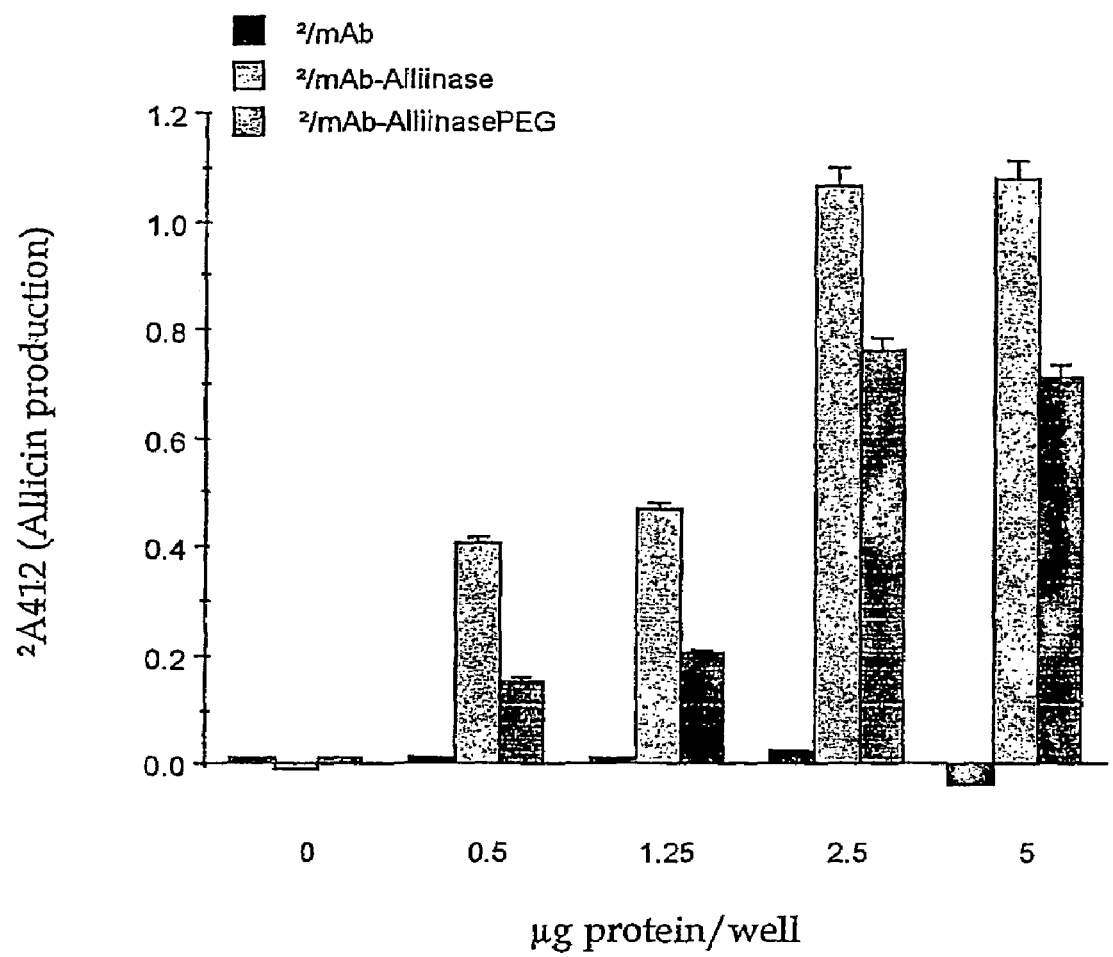
FIG. 4 shows determination of allicin produced as a function of different amounts of conjugates bound to CB-2 cells: mAb ErbB-2 (black columns); mAb ErbB-2 alliinase (light gray columns); mAb ErbB-2-alliinasePEG5000 (dark gray columns).

The production of allicin by mAb-alliinase conjugates specifically bound to the cultured cells was dependent on the concentration of the conjugate applied to the cultured cells. To determine the allicin produced as a function of different amounts of conjugates bound to cells, CB-2 cultured cells (10,000 cells/well) were grown overnight in 96-well plates, pre-fixed with 3% paraformaldehyde and washed with PBST. Fixed cells were treated with different amounts of mAb or conjugates (mAb-alliinase or mAb-alliinase PEG5000) for 1 hour at 37° C. The wells were washed (×3) with PBST and incubated with alliin (0.1 mg/ml, 0.1 ml/well) in $4\times10^{-4}$ M NTB in 50 mM phosphate buffer pH 7.4 containing 2 mM EDTA. Controls of fixed cells with alliin/NTB were used. Readings (A412) were done by Elisa Reader after 30 minutes. The results expressed as ΔA412 are shown in FIG. 4 wherein the black columns represent mAb ErbB-2, the light gray columns represent the mAb ErbB-2-alliinase conjugate and the dark gray columns the mAb ErbB-2-alliinasePEG5000 conjugate. These in vitro assays demonstrate the capacity of the conjugates mAb ErbB-2-alliinase and mAb ErbB-2-alliinasePEG5000 to produce allicin after binding to pre-fixed CB-2 cells.

Figure 5A:
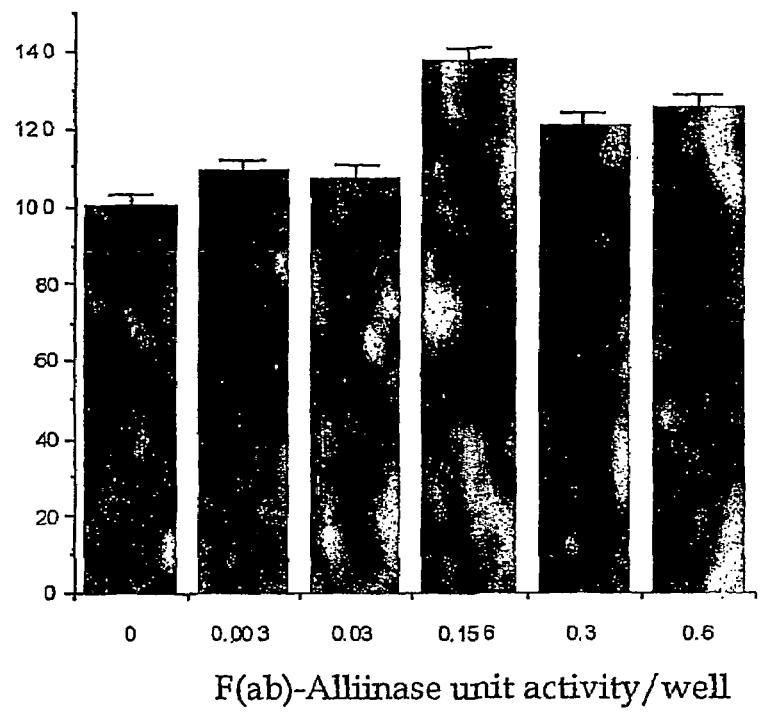
FIGS. 5A-5B show inhibition of [$^3$H]-thymidine incorporation into CB-2 cells upon treatment with conjugate of F(ab) ErbB-2-alliinase alone (FIG. 5A) or followed by the addition of alliin (FIG. 5B). Each treatment was conducted in triplicate.
Figure 5B:
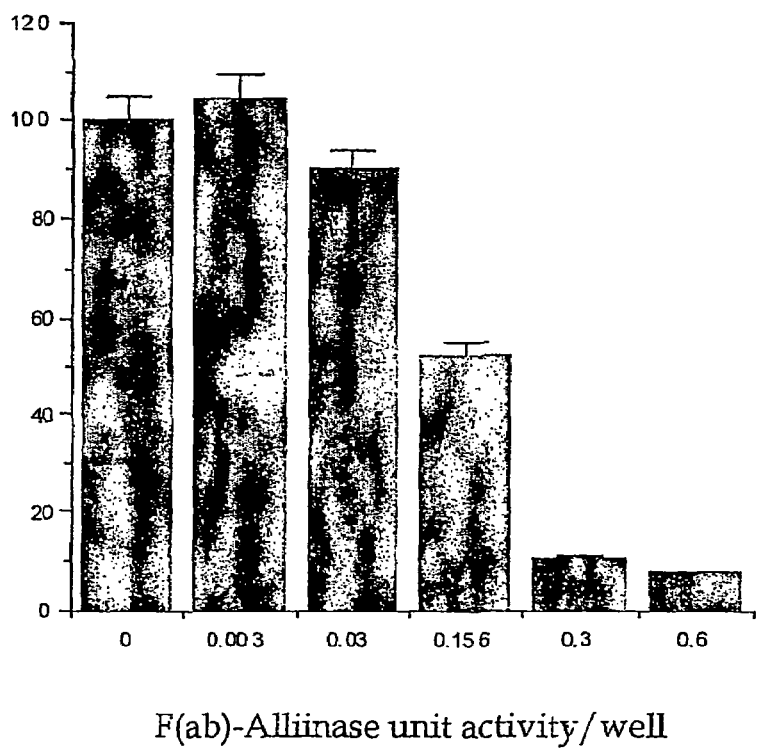

To determine the inhibition of [$^3$H]-thymidine incorporation into CB-2 cells upon treatment with conjugate F(ab)-alliinase followed by the addition of alliin, CB-2 cells (1,000 cells/well, 96-well plate) were grown for 6 hours at 37° C. in DMEM F12 medium with 10% iron-supplemented calf serum. Conjugate (F(ab)-alliinase) was added at various concentrations to the wells for 1 hour at 37° C. The wells were washed ×3 with the above medium and cultured for 16 hours with [$^3$H]-thymidine in the presence or absence of alliin (10 µg/well). The plate was frozen at −20° C., trypsinized and the cells harvested. For each treatment triplicates were done. FIG. 5 shows that inhibition of cell proliferation, as determined by [$^3$H]-thymidine incorporation into living CB-2 cells upon treatment with conjugates consisting of F(ab)-alliinase followed by the addition of alliin, was dependent on the amount of conjugate bound to the cells.

Example 4

Effect of Bound mAb and mAb-Alliinase Conjugate on Tissue Cultured Cells

The specific binding of mAb to ErbB-2-alliinase conjugate was investigated on cell cultures of human gastric tumor cells N87 which express the ErbB-2 receptor and on 32D cells, which are known to be devoid of the ErbB-2 receptors (Pinkas-Kramarski, 1996). Both types of cells were treated with either mAb ErbB-2 alone or its alliinase conjugate in the presence or absence of alliin and inhibition of [$^3$H]-thymidine incorporation in the cells was determined.

Figure 6:
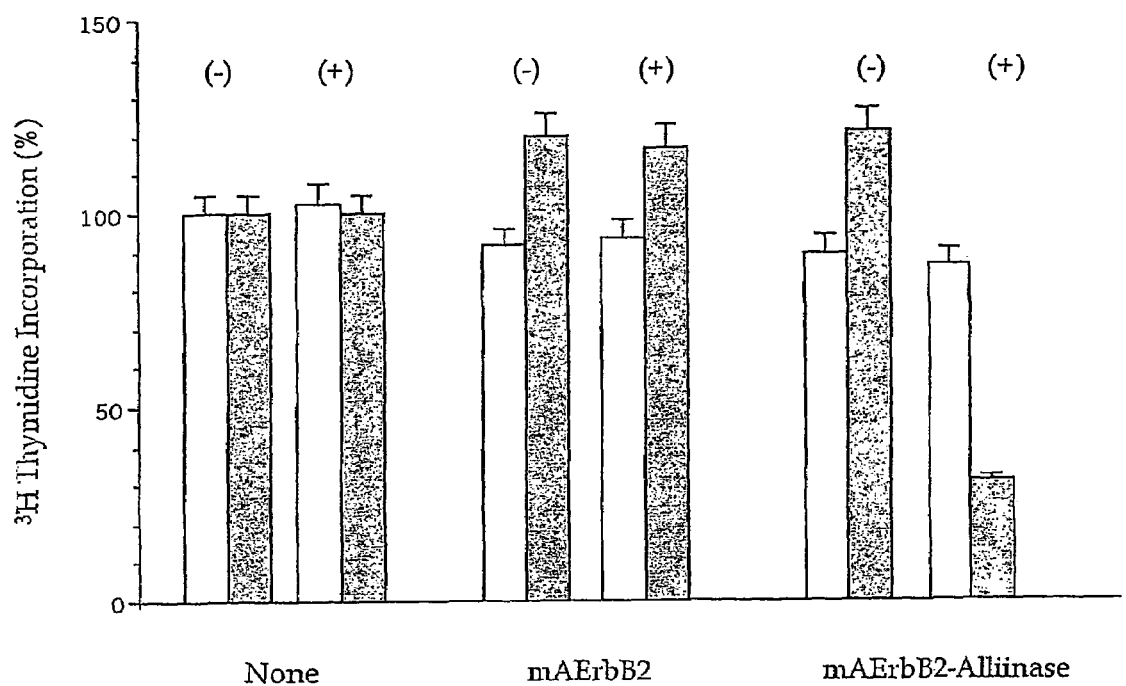
FIG. 6 shows inhibition of [$^3$H]-thymidine incorporation in 32D (blank columns) and N87 (gray columns) cells upon treatment with: none, mAbErbB-2-alone, or the conjugate mAbErbB-2-alliinase, in the absence (−) or presence (+) of added alliin. $^3$H thymidine incorporated into the DNA was determined. The experiments were conducted in triplicate.

Cell cultures of N87 (20,000 cells/well) were grown in 96-well plates and 32D cells were grown in suspension in 12-well plates (200,000 cells/ml). Cells were treated with: none, mAb ErbB-2 or mAb-ErbB-2-alliinase conjugate (total protein 2 µg/20,000 cells) for 1 hour at 37° C. The unbound proteins were then washed (×3) with medium (cells 32D were washed ×3 with medium by centrifugation and re-seeded in 96-well plates (20,000 cells/well). $^3$H -Thymidine (0.6 µCi/well) ±alliin (10 µg/well) were added to the wells. Cells were incubated at 37° C. for 16 hours. Cells were frozen at −20° C. (2 hours), trypsinized and harvested. $^3$H-Thymidine incorporated into the DNA was determined. The results depicted in FIG. 6 show that inhibition of [$^3$H]-thymidine incorporation in N87 cells treated with conjugate + alliin was >70% (gray columns) while no inhibition of incorporation was seen in 32D cells (blank columns) in the presence (+) or in the absence (−) of alliin. Moreover, N87 and CB-2 cells treated with mAb-alliinase and alliin for 16 hours were shown to be dead as they incorporated the vital dye Trypan blue (FIG. 7, right pictures).

Figure 7:
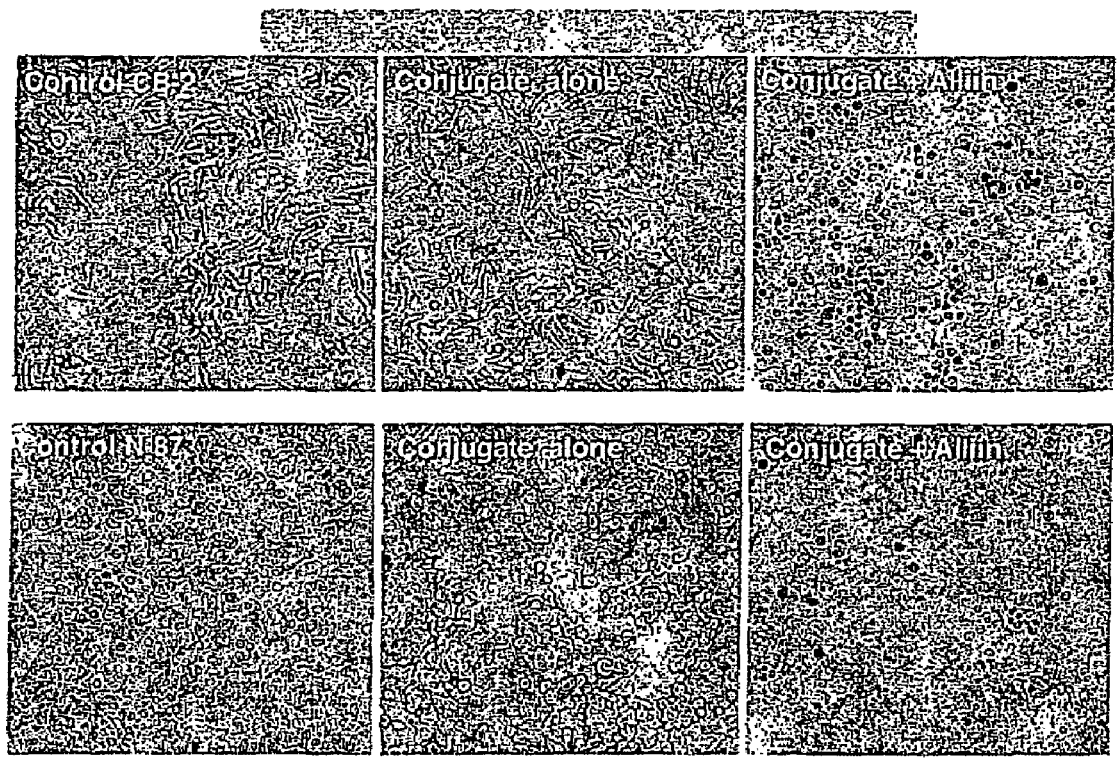
FIG. 7 shows the effect of mAb ErbB-2-alliinase conjugate on the viability of cultured CB-2-(upper pictures) and N87 (lower pictures) cancer cells in the presence or absence of alliin (×400). Staining was done with a 0.025% solution of Trypan Blue.

Cells which were treated only with alliin (without prior addition of the mAb-alliinase conjugate) or exposed only to-the anti-ErbB-2 mAb (±alliin) or to the mab-alliinase (without addition of alliin) were not damaged (FIG. 7, left and central pictures).

In Vivo Experiments with mAb-Alliinase Conjugates

Materials and Methods for the In Vivo Experiments

The preparation of mAb-alliinase conjugates was described in part 1 (in vitro experiments).

The following monoclonal antibodies (mAbs) were used for conjugation to alliinase:

N28 anti ErbB2 receptor (sub-clones 28.6 28.10) (Stancovski et al, 1991) were purified from ascites fluid by caprylic acid treatment followed by ammonium sulphate precipitation.

Rituxan, anti CD20, a commercial murine/human mAb was obtained from Genentech Inc. USA.

K768 Q527, anti-hepatitis C antibodies produced and supplied by XTL, Israel

The cancer cells used were N87 human gastric tumor cell line expressing the ErbB-2 receptors which have been described (Park et al, 1990). These cells were cultured, harvested and used for the production of tumors in animals.

The animals used were female CD1 (nude 5-7 weeks old) mice.

Radiolabeling of monoclonal antibodies was done with $^{125}$I using the chloramine-T method (0.5 mCi Na$^{125}$I/100 µg protein) according to (Hunter et al, 1962). The specific activity of free $^{125}$I-mAb and $^{25}$I-mAb-alliinase were 2.26 µCi/µg protein and 0.51 µCi/µg protein, respectively.

Clearance and organ distribution of $^{125}$I-mAb-alliinase conjugate were determined on cell N-87 treated nude mice (2-3 weeks old tumor). Mice were injected i.v. with 1×10$^6$ cpm $^{125}$I-mAb-alliinase conjugate; at various time intervals a mouse was sacrificed and samples (×3) from its isolated organs were counted for $^{125}$I radiolabeled content.

In Vivo Assay of Antitumor Effects

N-87 cultured cells (3-5×10$^6$) were injected subcutaneously into the back of the mice. One to 5 days later, groups of 6 to 8 mice received either none or mAb-alliinase conjugate by intravenous injection (20 µg mAb/mouse). Conjugates were injected with 3-4 days intervals.

All mice were supplemented with Pyridoxine (vitamin B$_6$) in the drinking water (100 mg/L). Every day mice were injected intraperitoneally (IP) two times with alliin (0.2 ml of 15 or 30 mg/ml) with a 7 hours interval and once with Pyridoxal 5-phosphate (0.2 ml, 20 mM in PBS/mouse). Tumor size was measured every second day.

Results

Example 5

Distribution and Clearance of Radiolabeled Anti-ErbB2 (Either as Free mAb or mAb-Alliinase Conjugate) in Mice Containing N-87 Induced Tumors Tumors were generated in Female CDI nude mice by subcutaneous injection of human gastric tumor cells (10×10$^6$) N-87. Two to three weeks later mice were injected intravenously with either $^{125}$I-mAb anti-ErbB2 or $^{125}$-conjugated alliinase-mAb anti-ErbB2. At various time intervals mice were sacrificed and samples from various organs were analyzed for their $^{125}$I radioactive content.

Figure 9A:
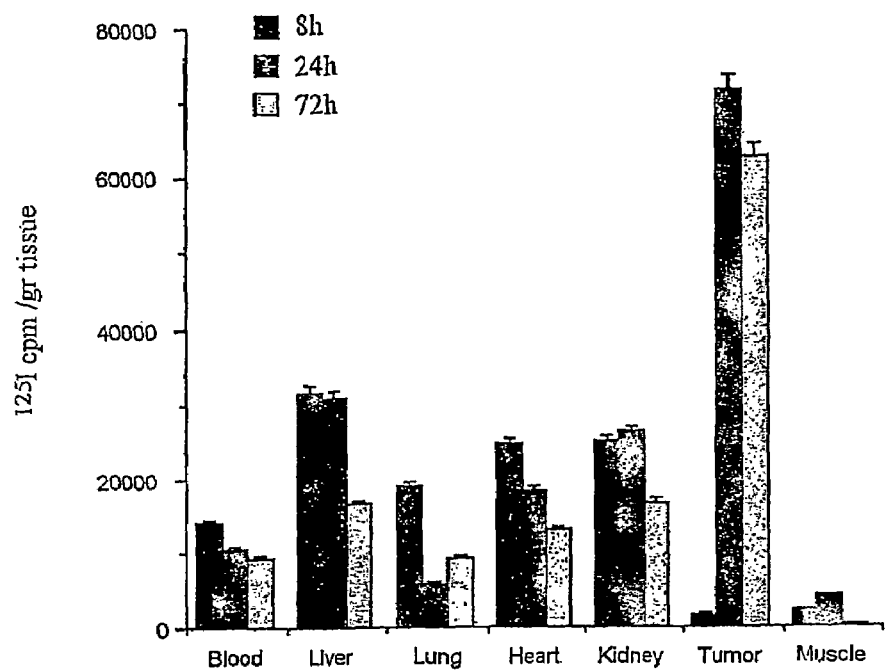
FIG. 9A shows the distribution of $^{125}$I-anti ErbB2 monoclonal antibodies in organs of mice pretreated with N-87 tumor cells. Treated mice were sacrificed after 8, 24 and 72 hours.
Figure 9B:
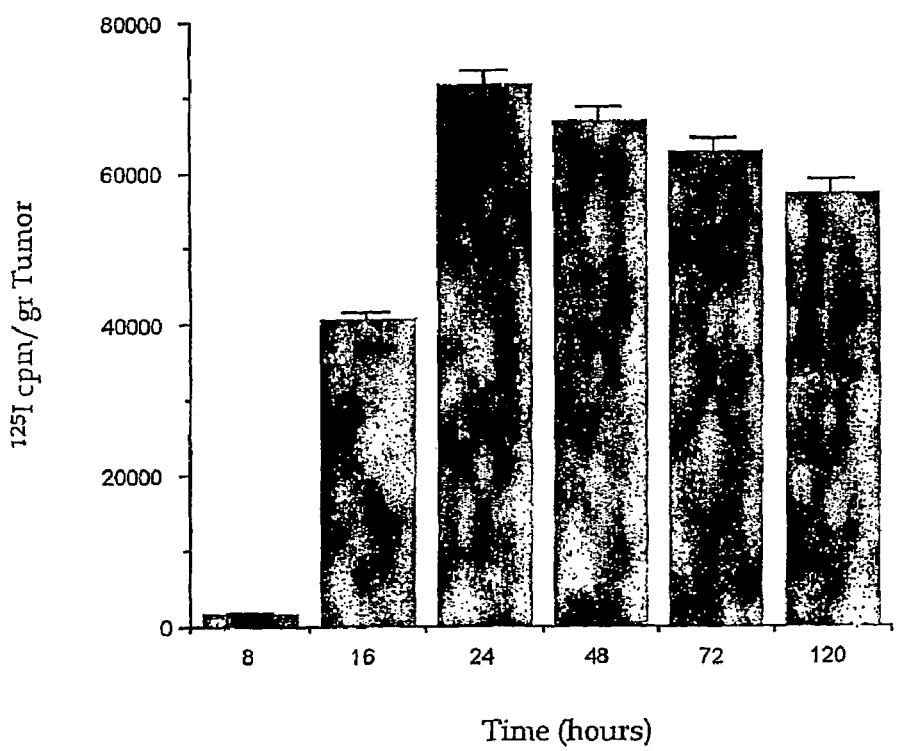
FIG. 9B shows the accumulation of $^{125}$I mAb-alliinase conjugate in the tumors at 8, 16, 24, 48, 72 and 120 hours.
Figure 10:
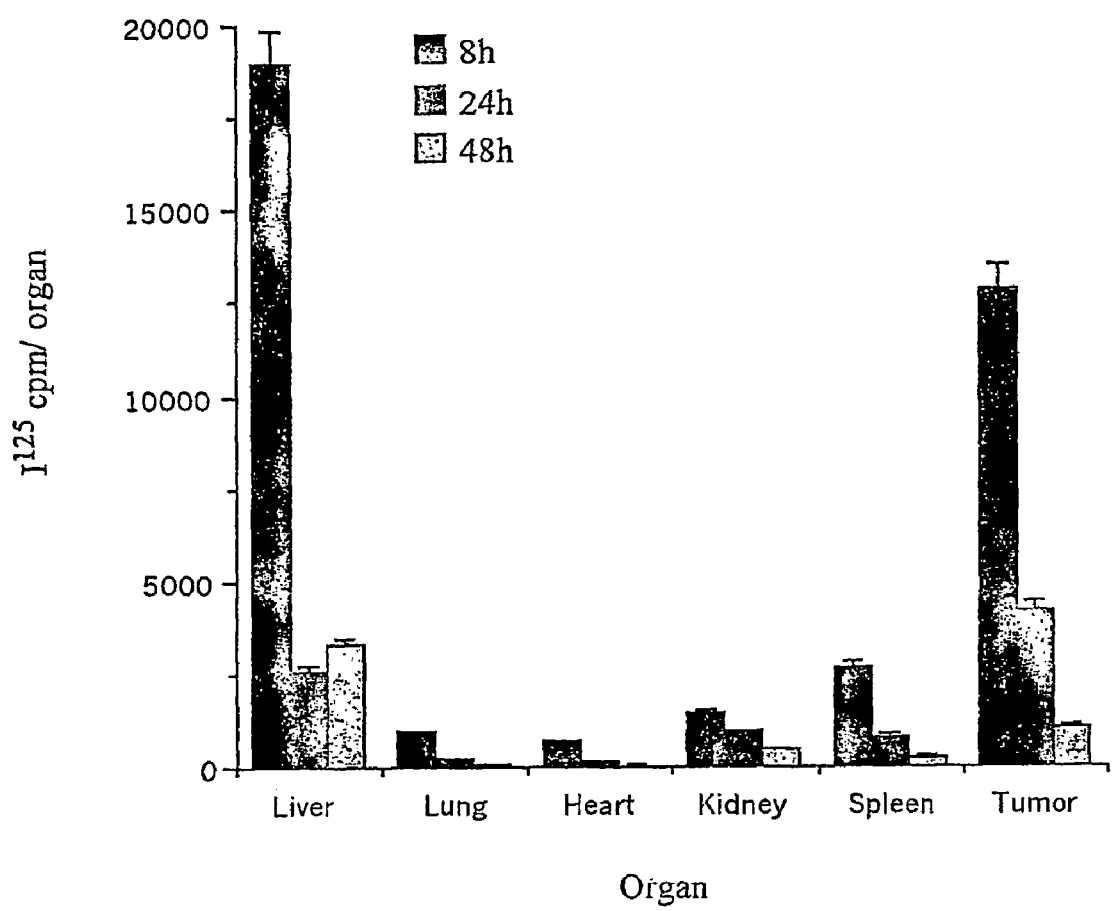
FIG. 10 shows distribution of $^{125}$I-anti ErbB2-alliinase conjugate in organs of mice pretreated with N-87 cells. Treated mice were sacrificed after 8, 24, and 48 hours.

The accumulation pattern in various organs of the free mAb or the mAb-alliinase-conjugate is shown in FIG. 9A and FIG. 10, respectively. In both cases there is a specific accumulation of the $^{125}$I-labeled protein in the tumor compared to other organs. The kinetics of the accumulation and the clearance of $^{125}$I-mAb anti-ErbB2 is shown in FIG. 9B. The maximal binding of the free mAb was seen after about 24 hours (FIGS. 9A and 9B), whereas the binding of the conjugate reached its maximum in about 8 hours (FIG. 10).

Example 6

Effect of Alliin Administration, in Mice Treated with mAb-Alliinase Conjugate, on Their Tumor Volume The conjugate used for these experiments was mAb anti ErbB2 (N28) coupled to alliinase as described before.

All the animal groups were injected with N-87 cells 1-5 days before any treatment.

Group 1. Mice were treated either with alliin alone or untreated.

Group 2. Mice were treated with mAb-alliinase conjugates only, without administration of the substrate alliin.

Group 3. Mice were treated with mAb-alliinase conjugates and alliin was administered regularly as described below.

MAb-alliinase conjugate was injected I.V. every 3-4 days. Mice were treated ×5 with the conjugate (20 μg/mouse) in 3-4 day intervals. Total amount of mAb in the conjugate/mouse was 0.1 mg. Alliin was injected (I.P.) 5 hours after the conjugate administration and in the other days twice a day (7 hours interval) as was described in Materials and Methods.

Figure 11:
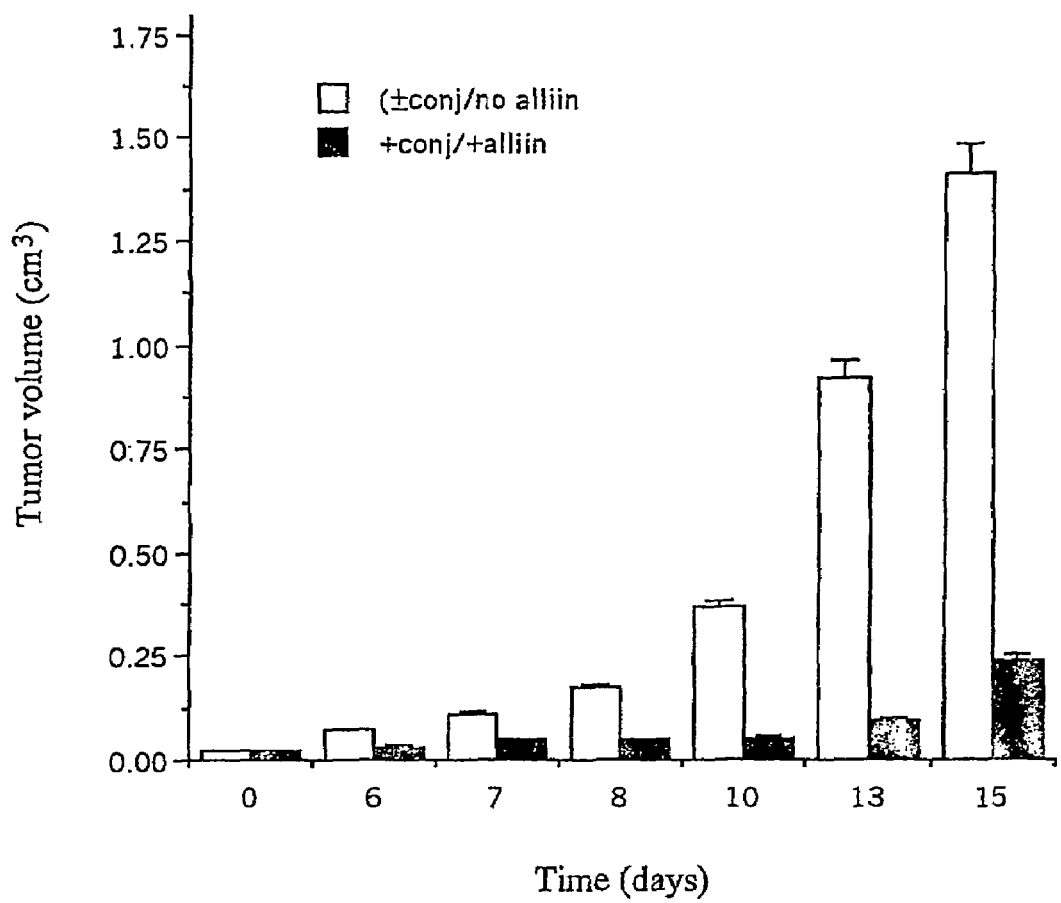
FIG. 11 shows the effect of conjugated alliinase-mAb N-28±alliin on tumor growth in mice pre-treated with N-87 cancer cells. Mice treated with mAb-Alliinase conjugates without administration of alliin ☐; with administration of alliin ■.

The kinetics of tumor growth was similar in untreated mice or in mice treated with the mAb-alliinase conjugate but without administration of alliin (Groups 1 and 2). Alliin itself had no effect on the tumor size of control mice (results not shown). In some experiments the growth of the non-treated mice was to some extent lower than that of mice treated with only the mAb-alliinase conjugate. However the growth of the tumors in mice which received the injected mab-alliinase conjugates followed by successive administrations of the substrate alliin were very significantly lower (FIG. 11). Conclusions The results obtained from both the in vitro and in vivo experiments confirmed that a monoclonal antibody conjugated to alliinase can specifically deliver and target the enzyme alliinase to the tumor. The subsequent administration of the alliinase substrate, alliin, to the treated mice, causes its in situ conversion into allicin, which inhibits the tumor growth. Since mammalian cells do not produce such a type of lyase as alliinase, the alliin administrated either per os or intraperitoneally or intravenously will be converted to allicin only by the alliinase, which is chemically ligated to the mAb which is bound to the tumor cells. The above-described experiments clearly show that the enzymatic activity of alliinase in the mAb-alliinase conjugate enables the continuous generation of allicin at the target site in vivo and the anti-tumor effect is dependent on the administration of the substrate alliin.

This same principle can be used to inhibit the growth of any other types of malignant cells or offending pathogens. The only requirement is the availability of highly specific monoclonal antibodies or other types of carriers specific for different targets, which can be chemically or by recombinant fusion synthesis ligated to alliinase to form the desired conjugate. Some such examples are:

mAbs against hepatitis viruses or other retroviruses such as HIV etc.

mAbs against a variety of markers on a surface of cancer cells and metastatic antigens mAbs against fungi such as *Candida albicans*, Micoplasma, etc.

mAbs against bacterial infections such as Staphylococci or Streptococci causing bacteremia, etc.

mAbs against parasites which appear in the circulation (*Trypanosomes, Plasmodium* etc.)

Soluble cytokines or ligands to specific receptors on target cells.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

REFERENCES

Abramovitz et al, "Allicin-induced decrease in formation of fatty streaks (atherosclerosis) in mice fed on a cholesterol-rich diet", *Coronary Artery Dis* 10:515-519 (1999)

Augusti et al, "Lipid lowering effect of allicin (diallyl disulphide-oxide) on long term feeding to normal rats", *Experientia* 30:468-470 (1974)

Bacus S, "Methods and Compositions for Cancer Therapy and for Prognosticating Responses to Cancer Therapy", U.S. Pat. No. 5,514,554, issued May 7, 1996

Bagshawe K D, "Cytotoxic Drug Therapy", U.S. Pat. No. 6,299,876, issued Oct. 9, 2001

Better et al, "*Escherichia coli* secretion of an active chimeric antibody fragment", *Science* 240:1041-1043 (1988)

Bordia et al, "The protective action of essential oils of onion and garlic in cholesterol-fed rabbits", *Atherosclerosis* 22: 103-109 (1975)

Bordia et al, "Effect of essential oil of garlic on serum fibrinolytic activity in patients with coronary artery disease", *Atherosclerosis* 28:155-159 (1977)

Bordia et al, "Effect of garlic feeding on regression of experimental atherosclerosis in rabbits", *Artery* 7:428-437 (1980)

Boulianne et al, "Production of functional chimaeric mouse/human antibody", *Nature* 312:643-646 (1984)

Cabilly et al, "Generation of antibody activity from immunoglobulin polypeptide chains produced in *Escherichia coli.*" *Proc Natl Acad Sci USA* 81:3273-3277 (1984)

Cabilly et al, "Recombinant immunoglobin preparations" U.S. Pat. No. 4,816,567, issued Mar. 28, 1989; and "Recombinant immunoglobulin preparations, methods for their preparation, DNA sequences, expression vectors and recombinant host cells therefor", European patent 0 125 023, published Nov. 14, 1984

Carlsson et al, "Protein thiolation and reversible protein-protein conjugation", *Biochem J* 173:723-737 (1978)

Chang, T W, "Methods and Substances for Recruiting Therapeutic Agents to Solid Issues Comprising Two Single Chain VH-VL Bifunctional Binding Molecules", European patent 0 506 124, published Sep. 30, 1992

Colligan et al, *Current Protocols in Immunology*, Green Publishing Assoc., and Wiley Interscience, New York (2001)

David et al, "Immunometric assays using monoclonal antibodies", U.S. Pat. No. 4,376,110, issued Mar. 8, 1983

Degani et al, "Selective cyanylation of sulfhydryl groups. II On the synthesis of 2-nitro-5-thiocyanatobenzoic acid", *J Org Chem* 36:2727-2728 (1971)

Eilat et al, "Alteration of lipid profile in hyperlipidemic rabbits by allicin, an active constituent of garlic", *Coronary Artery Dis* 6:985-990 (1995)

Epstein et al, "Vasopermeability Enhancing Peptide of Human Interleukin-2 and Immunoconjugates Thereof", U.S. Pat. No. 6,008,319, issued Dec. 28, 1999

Eshhar et al, "Chimeric T cell receptor which incorporates the anti-tumour specificity of a monoclonal antibody with the cytolytic activity of T cells: a model system for immunotherapeutical approach", *Br J Cancer Suppl*, 10:27-29 (1990)

Fell, Jr. et al, "Therapeutic Antibody Based Fusion Proteins", U.S. Pat. No. 5,645,835, issued Jul. 8, 1997

Fitzgerald et al, "Recombinant Antibody-Toxin Fusion Protein", U.S. Pat. No. 5,863,745, issued Jan. 26, 1999

George et al, "Methods of Delivering Agents to Target Cells", U.S. Pat. No. 5,861,156, issued Jan. 19, 1999

Greenfield et al, "Anthracycline Conjugates Having a Novel Linker and Methods for Their Production", U.S. Pat. No. 5,122,368, issued Jun. 16, 1992

Griffiths et al, "Delivery of Diagnostic and Therapeutic Agents to a Target Site", U.S. Pat. No. 5,965,131, issued Oct. 12, 1999

Gross et al, "Expression of immunoglobulin-T-cell receptor chimeric molecules as functional receptors with antibody-type specificity", *Proc Natl Acad Sci USA*, 86:10024-10028 (1989)

Harlow et al, *Antibodies: A Laboratory Manual*, Cold Spring Harbor Laboratory, Cold Spring Harbor, N.Y. (1988)

Hirsh et al, "The effect of purified allicin, the major ingradient of freshly crushed garlic on cancer cell proliferation", *Nutrition and Cancer* 35:245-254 (2000)

Hunter et al, "Preparation of iodine-131 labeled human growth hormone of high activity", *Nature* 194:495-496 (1962)

Hurwitz et al, "Suppression and promotion of tumor growth by monoclonal antibodies to ErbB-2 differentially correlate with cellular uptake", *Proc Natl Acad Sci USA* 92:3353-3357 (1995)

Huston et al, "Biosynthetic antibody binding sites", U.S. Pat. No. 5,091,513, issued Feb. 25, 1992

Iwasa et al, Biospecific Antibody to Cancer Cell and Enzyme with Prodrug-Activating Characteristics", international publication WO 91/09134, published Jun. 27, 1991

Jin et al, "Identification of an Essential Tryptophan Residue in Alliinase from Garlic (*Allium sativum*) by Chemical Modidfication, *Bull Korea Chem Soc* 22(1):68-76 2001

Kamisaki et al, "Reduction in immunogenicity and clearance rate of *Escherichia coli* L-asparaginase by modification with monomethoxypolyethylene glycol", *J Pharmacol Exp Ther* 216:410-414 (1981)

Kaneko et al, "Bifunctional Linking Compunds, Conjugates and Methods for Their Production", U.S. Pat. No. 5,137,877, issued Aug. 11, 1992

Kieswetter et al, "Effect of garlic on blood fluidity and fibrinolytic activity: a randomised placebo controlled doubleblind study", *Br J Pract* 69:24-29 (1990)

Knipschid et all, "Garlic, onions and cardiovascular risk factor: A review of the evidence from human experiments. Emphasis on commercially available preparations", *Br J Clin Pharmacol* 28:535-544 (1989)

Kohler et al, "Continuous cultures of fused cells secreting antibody of predefined specificity", *Nature* 256:495-497 (1975)

Kudo et al, "Mouse-human chimaeric immunoglobulin heavy chain specific for the call antigen", European patent 0 184 187, published Jun. 11, 1986

Ladner et al, "Single polypeptide chain binding molecules", U.S. Pat. No. 4,946,778, issued Aug. 7, 1990

Ladner et al, "Generation and selection of novel DNA-binding proteins and polypeptides", U.S. Pat. No. 5,096,815, issued Mar. 17, 1992

Liu et al, "Chimeric mouse-human IgG1 antibody that can mediate lysis of cancer cells", *Proc Natl Acad Sci USA*. 1987 May;84(10):3439-3443 (1987)

Makheja et al, "Antiplatelet constituents of garlic and onion", *Agents Actions* 29:360-363 (1990)

Manabe et al, in *Sulfur Nutrition and Sulfur Assimilation in Higher Plants*, Brunold et al (eds.), Paul Haupt, Berne (2000), pp. 419-420

McKinney et al, "A simple, non-chromatographic procedure to purify immunoglobulins from serum and ascites fluid", *J Immunol Methods* 96:271-278 (1987)

Meinkoth et al, "Hybridization of nucleic acids immobilized on solid supports", *Anal Biochem* 138:267-284 (1984)

Miron et al, "A simplified method for the preparation of succinimidyl carbonate polyethylene glycol for coupling to proteins", *Bioconj Chemistry* 4:568-569 (1993)

Miron et al, "Immobilized Alliinase and Continuous Production of Allicin", international patent WO 97/39115, published Oct. 23, 1997

Miron et al, "A spectrophotometric assay for allicin and alliinase (Alliin lyase) activity: reaction of 2-nitro-5-thiobenzoate with thiosulfinates". *Anal Biochem* 265:317-325 (1998)

*Monoclonal Antibody Index, Vol 1: Cancer*, 4$^{th}$ edition (e-book located at www.gallartinternet.com/mai), ISBN: 84-88447-05-1, Gallart Biotech, Barcelona, Spain (2001)

*Monoclonal Antibody Index, Vol 2: Transplant, Infection and Heart*, 2$^{nd}$ edition (e-book located at www.gallartinternet.com/mai), ISBN: 94-88447-07-8, Gallart Biotech, Barcelona, Spain (2001)

Morrison et al, "Chimeric human antibody molecules: mouse antigen-binding domains with human constant region domains". *Proc Natl Acad Sci USA* 81:6851-6855 (1984)

Morrison et al, "Chimeric receptors by DNA splicing and expression" European patent 0 173 494, published Mar. 5, 1986

Nag et al, "A calorimetric assay for estimation of polyethylene glycol and polyethylene glycolated protein using ammonium ferrothiocyanate", *Anal Biochem* 237:224-231 (1996)

Neuberger et al, "A hapten-specific chimaeric IgE antibody with human physiological effector function", *Nature* 314:268-270 (1985)

Neuberger et al, "Production of Chimeric Antibodies", international patent WO 86/01533, published Jan. 14, 1987

Park et al, "Characteristics of cell lines established from human gastric carcinoma", *Cancer Research* 50:2773-2780 (1990)

Pinkas-Kramarski et al, "Diversification of Neu differentiation factor and epidermal growth factor signaling by combinatorial receptor interactions", *EMBO J* 15:2452-2467 (1996)

Rabinkov et al, "Alliinase (Alliin Lyase) from Garlic (*Allium-Sativum*) Is Glycosylated at Asn(146) and Forms a Complex with a Garlic Mannose-Specific Lectin", *Glycoconj J* 12:690-698 (1995)

Robinson et al, "Modular Assembly of Antibody Genes, Antibodies Prepared Thereby and Use", international patent WO 87/02671, published May 7, 1987

Sahagan et al, "A genetically engineered murine/human chimeric antibody retains specificity for human tumor-associated antigen" *J Immunol* 137:1066-1074 (1986)

Sela et al, "Methods and Compositions for Cancer Therapy and for Prognosticating Responses to Cancer Therapy", European patent 0 554 441, published Jan. 27, 1999)

Senter et al, "Antibody-Enzyme Conjugates in Combination with Prodrugs for the Delivery of Cytotoxic Agents to Tumor Cells", European patent 0 302 473, published Feb. 8, 1989

Stancovski et al, "Mechanistic aspects of the opposing effects of monoclonal antibodies to the ERBB2 receptor on tumor growth", *Proc Natl Acad Sci USA* 88:8691-8695 (1991)

Stoll et al, "Chemical investigation on alliin, the specific pinciple of garlic", *Adv Enzymol* 11:377-400 (1951)

Sun et al, "Chimeric antibody with human constant regions and mouse variable regions directed against carcinoma-associated antigen 17-1A", *Proc Natl Acad Sci USA* 84:214-218 (1987)

Taniguchi et al, "Process for the production of a chimera monoclonal antibody" European patent 0 171 496, published Feb. 19, 1986

Thorpe et al, Cancer Treatment Methods Using Therapeutic Conjugates that Bind to Aminophospholipids", U.S. Pat. No. 6,312,694, issued Nov. 6, 2001

Tzahar et al, "A Hierarchial network of interreceptor interactions determines signal transduction by Neu differentiation factor/Neuregulin and Epidermal Growth Factor", *Mol Cell Biol* 16:5276-5287 (1996)

Van Damme et al, "Isolation and characterization of alliinase cDNA clones from garlic (*Allium sativum L.*) and related species", *Eur J Biochem* 209(2):751-757 (1992)

What is claimed is:

1. A conjugate of alliinase, in an enzymatically active form, with an antibody, wherein said conjugate binds to a cell or to a microorganism of interest in the body of a mammal.

2. A conjugate according to claim 1, wherein the alliinase is recombinant.

3. A conjugate according to claim 1, wherein the alliinase is onion or garlic alliinase.

4. A conjugate according to claim 3, wherein the alliinase is garlic alliinase.

5. A conjugate according to claim 1, wherein the antibody is a cell- or tissue-specific monoclonal antibody or an antigen-binding fraction thereof.

6. A conjugate according to claim 5, wherein said cell- or tissue-specific monoclonal antibody or antigen-binding fraction thereof recognizes a specific receptor on the cell surface.

7. A conjugate according to claim 6, wherein said monoclonal antibody is of human or animal origin.

8. A conjugate according to claim 6, wherein said monoclonal antibody is a recombinant or humanized antibody.

9. A conjugate according to claim 5, wherein said antibody comprises an antigen-binding fraction of a cell- or tissue-specific monoclonal antibody, said fraction being a $F(ab)_2$ dimer, F(ab) monomer, FV, or a single chain.

10. A conjugate according to claim 5, wherein said monoclonal antibody or antigen-binding fraction thereof recognizes a specific antigen on the surface of cancer cells.

11. A conjugate according to claim 10, wherein said monoclonal antibody recognizes the ErbB-2 receptor on the surface of cancer cells.

12. A conjugate according to claim 1, wherein the alliinase is pegylated.

13. A pharmaceutical composition comprising a conjugate according to claim 1 and a pharmaceutically acceptable carrier.

14. A pharmaceutical kit comprising, in separate compartments, a pharmaceutical composition according to claim 13 and a composition of alliin.

15. A kit in accordance with claim 14, further including instructions for administration of the two compositions.

16. A method for killing or inhibiting the growth of mammalian cells that express a cell-type specific protein or cancer antigen, comprising administering a conjugate of alliinase and an antibody that binds to said cell-type specific protein or cancer antigen, followed by administration of alliin, whereby the alliinase of the conjugate converts alliin to allicin and the allicin kills the cells or inhibits cell growth.

17. A method according to claim 16, wherein the mammalian cells are cancer cells.

* * * * *

UNITED STATES PATENT AND TRADEMARK OFFICE
CERTIFICATE OF CORRECTION

| | |
|---|---|
| PATENT NO. | : 7,445,802 B2 |
| APPLICATION NO. | : 10/451849 |
| DATED | : November 4, 2008 |
| INVENTOR(S) | : Rabinkov et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1212 days.

Signed and Sealed this
Eleventh Day of January, 2011

David J. Kappos
*Director of the United States Patent and Trademark Office*